US011045650B2

(12) United States Patent
Brink et al.

(10) Patent No.: US 11,045,650 B2
(45) Date of Patent: Jun. 29, 2021

(54) HIGH FREQUENCY NEUROSTIMULATION FOR PELVIC SYMPTOM CONTROL

(71) Applicant: Medtronic, Inc., Minneapolis, MN (US)

(72) Inventors: Thaddeus S. Brink, St. Paul, MN (US); Dwight E. Nelson, Shoreview, MN (US); Lance Zirpel, Lino Lakes, MN (US); Xin Su, Plymouth, MN (US); Blake A. Hedstrom, Minneapolis, MN (US); Erik J. Peterson, Fridley, MN (US); David A. Dinsmoor, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/831,986

(22) Filed: Dec. 5, 2017

(65) Prior Publication Data

US 2018/0154144 A1    Jun. 7, 2018

Related U.S. Application Data

(60) Provisional application No. 62/430,498, filed on Dec. 6, 2016.

(51) Int. Cl.
*A61N 1/36* (2006.01)
*A61B 5/20* (2006.01)
(Continued)

(52) U.S. Cl.
CPC .......... *A61N 1/36007* (2013.01); *A61B 5/202* (2013.01); *A61B 5/6874* (2013.01);
(Continued)

(58) Field of Classification Search
CPC .............. A61N 1/36007; A61N 1/0514; A61N 1/3606; A61N 1/36132; A61N 1/36064;
(Continued)

(56) References Cited

U.S. PATENT DOCUMENTS 4,338,945 A    7/1982 Kosugi et al.
4,541,432 A    9/1985 Molina-Negro et al.
(Continued)

FOREIGN PATENT DOCUMENTS

CN    107050645 A    8/2017
EP      2396072 B1    3/2013
(Continued)

OTHER PUBLICATIONS

Notice of Allowance from U.S. Appl. No. 15/967,329, dated Jan. 28, 2019, 7 pp.
(Continued)

*Primary Examiner* — Tammie K Marlen
(74) *Attorney, Agent, or Firm* — Shumaker & Sieffert, P.A.

(57) ABSTRACT

In general, techniques, methods, systems, and devices for delivering high frequency neurostimulation to control one or more pelvic disorders are described. In one example, a method includes identifying, by a medical device configured to be at least partially implanted in a patient, an indication to inhibit bladder activity. The medical device generates, in response to identifying the indication, electrical stimulation therapy comprising first electrical stimulation pulses comprising a first frequency greater than or equal to about 500 Hertz and less than or equal to about 5,000 Hertz. Further, the medical device delivers the electrical stimulation therapy to a target nerve selected from a group consisting of: a sacral nerve, a pelvic nerve, a tibial nerve, and a pudendal nerve of the patient.

20 Claims, 13 Drawing Sheets

(51) Int. Cl.
  *A61B 5/00* (2006.01)
  *A61N 1/372* (2006.01)
  *A61B 5/11* (2006.01)
  *A61B 5/391* (2021.01)

(52) U.S. Cl.
  CPC ..... *A61N 1/36064* (2013.01); *A61N 1/36107* (2013.01); *A61N 1/36139* (2013.01); *A61N 1/36171* (2013.01); *A61B 5/1113* (2013.01); *A61B 5/1116* (2013.01); *A61B 5/391* (2021.01); *A61B 5/4836* (2013.01); *A61N 1/36067* (2013.01); *A61N 1/36132* (2013.01); *A61N 1/36178* (2013.01); *A61N 1/37205* (2013.01)

(58) Field of Classification Search
  CPC ............ A61N 1/36107; A61N 1/36139; A61N 1/36171; A61N 1/36067; A61N 1/36178; A61N 1/37205; A61B 5/202; A61B 5/6874; A61B 5/04882; A61B 5/1113; A61B 5/1116; A61B 5/4836
  See application file for complete search history.

(56) References Cited

U.S. PATENT DOCUMENTS

| | | | |
|---|---|---|---|
| 5,603,726 | A | 2/1997 | Schulman et al. |
| 5,800,465 | A | 9/1998 | Thompson et al. |
| 6,289,247 | B1 | 9/2001 | Faltys et al. |
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,050,856 | B2 | 5/2006 | Stypulkowski |
| 7,263,402 | B2 | 8/2007 | Thacker et al. |
| 7,333,858 | B2 | 2/2008 | Killian et al. |
| 7,571,001 | B2 | 8/2009 | Thacker et al. |
| 7,577,480 | B2 | 8/2009 | Zeijlemaker |
| 7,657,318 | B2 | 2/2010 | King et al. |
| 7,689,289 | B2 | 3/2010 | King |
| 7,742,810 | B2 | 6/2010 | Moffitt et al. |
| 8,359,103 | B2 | 1/2013 | Alataris et al. |
| 8,504,150 | B2 | 8/2013 | Skelton |
| 8,620,441 | B2 | 12/2013 | Greenberg et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 8,788,048 | B2 | 7/2014 | Bennett et al. |
| 8,923,988 | B2 | 12/2014 | Bradley |
| 9,002,460 | B2 | 4/2015 | Parker |
| 9,138,582 | B2 | 9/2015 | Doan et al. |
| 9,155,892 | B2 | 10/2015 | Parker et al. |
| 9,186,510 | B2 | 11/2015 | Gliner et al. |
| 9,339,655 | B2 | 5/2016 | Carbunaru |
| 9,358,391 | B2 | 6/2016 | Zhu et al. |
| 9,381,356 | B2 | 7/2016 | Parker et al. |
| 9,381,360 | B2 | 7/2016 | Hershey |
| 9,386,934 | B2 | 7/2016 | Parker et al. |
| 9,604,058 | B2 | 3/2017 | Moffitt |
| 9,707,394 | B2 | 7/2017 | Bennett, II et al. |
| 9,789,306 | B2 | 10/2017 | Sabourin et al. |
| 9,808,627 | B2 | 11/2017 | Gliner et al. |
| 9,827,422 | B2 | 11/2017 | Zhu |
| 9,950,165 | B2 | 4/2018 | Howard |
| 10,118,036 | B2 | 11/2018 | Zhu |
| 10,118,038 | B2 | 11/2018 | De Ridder |
| 10,207,109 | B2 | 2/2019 | Zhu et al. |
| 10,213,605 | B2 | 2/2019 | Grill et al. |
| 10,315,031 | B2 | 6/2019 | Brink et al. |
| 2002/0127144 | A1 | 9/2002 | Mehta |
| 2004/0267333 | A1 | 12/2004 | Kronberg |
| 2005/0070987 | A1 | 3/2005 | Erickson |
| 2007/0067004 | A1 | 3/2007 | Boveja et al. |
| 2007/0100388 | A1 | 5/2007 | Gerber |
| 2007/0244522 | A1 | 10/2007 | Overstreet |
| 2007/0255364 | A1 | 11/2007 | Gerber et al. |
| 2008/0269833 | A1 | 10/2008 | Scott et al. |
| 2009/0036945 | A1 | 2/2009 | Chancellor et al. |
| 2009/0131993 | A1 | 5/2009 | Rousso et al. |
| 2009/0222053 | A1 | 9/2009 | Gaunt et al. |
| 2010/0121416 | A1 | 5/2010 | Lee |
| 2010/0152807 | A1 | 6/2010 | Grill et al. |
| 2010/0222686 | A1 | 9/2010 | Fisher et al. |
| 2010/0228079 | A1 | 9/2010 | Forsell |
| 2011/0054570 | A1 | 3/2011 | Lane |
| 2011/0071589 | A1 | 3/2011 | Starkebaum et al. |
| 2011/0093041 | A1 | 4/2011 | Straka et al. |
| 2011/0125223 | A1 | 5/2011 | Carbunaru et al. |
| 2011/0282412 | A1 | 11/2011 | Glukhovsky et al. |
| 2012/0101326 | A1* | 4/2012 | Simon ................ A61N 1/36007 600/9 |
| 2012/0130444 | A1 | 5/2012 | Wei et al. |
| 2012/0155188 | A1 | 6/2012 | Buettner et al. |
| 2012/0197336 | A1 | 8/2012 | Su |
| 2012/0197337 | A1* | 8/2012 | Su ...................... A61N 1/36007 607/41 |
| 2012/0277621 | A1 | 11/2012 | Gerber et al. |
| 2012/0296389 | A1 | 11/2012 | Fang et al. |
| 2013/0110194 | A1 | 5/2013 | Wei |
| 2013/0208390 | A1 | 8/2013 | Singh et al. |
| 2013/0238066 | A1 | 9/2013 | Boggs, II et al. |
| 2013/0268021 | A1 | 10/2013 | Moffitt |
| 2013/0289664 | A1 | 10/2013 | Johanek |
| 2013/0293025 | A1 | 11/2013 | Xu et al. |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074186 | A1 | 3/2014 | Faltys et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0243924 | A1 | 8/2014 | Zhu et al. |
| 2014/0296936 | A1 | 10/2014 | Alataris et al. |
| 2014/0371813 | A1 | 12/2014 | King et al. |
| 2014/0379043 | A1 | 12/2014 | Howard |
| 2015/0127062 | A1 | 5/2015 | Holley et al. |
| 2015/0179177 | A1 | 6/2015 | Nagao |
| 2015/0217117 | A1 | 8/2015 | Hershey |
| 2016/0030741 | A1 | 2/2016 | Wei et al. |
| 2016/0136420 | A1 | 5/2016 | Brink et al. |
| 2016/0346546 | A1 | 12/2016 | Zhu |
| 2017/0028201 | A1 | 2/2017 | Howard |
| 2017/0209695 | A1 | 7/2017 | Solomon |
| 2017/0312523 | A1 | 11/2017 | Bennett et al. |
| 2018/0154144 | A1 | 6/2018 | Brink et al. |
| 2018/0289965 | A1 | 10/2018 | Nelson et al. |
| 2019/0001139 | A1 | 1/2019 | Mishra et al. |
| 2019/0038901 | A1 | 2/2019 | Zhu |
| 2020/0346018 | A1 | 11/2020 | Grill et al. |

FOREIGN PATENT DOCUMENTS

| | | |
|---|---|---|
| EP | 2813262 B1 | 10/2015 |
| WO | 2002009808 A1 | 2/2002 |
| WO | 2010058178 A1 | 5/2010 |
| WO | 2010123704 A2 | 10/2010 |
| WO | 2011156286 A2 | 12/2011 |
| WO | 2015179177 A1 | 11/2015 |
| WO | 2015179281 A1 | 11/2015 |
| WO | 2016127130 A1 | 8/2016 |
| WO | 2016191055 A1 | 12/2016 |
| WO | 2017106503 A1 | 6/2017 |
| WO | 2017214638 A1 | 12/2017 |

OTHER PUBLICATIONS

International Search Report and Written Opinion of International Application No. PCT/US2017/064925, dated Apr. 11, 2018, 14 pp.

(56) References Cited

OTHER PUBLICATIONS

Warman et al., "Modeling the Effects of Electric Fields on Nerve Fibers: Determination of Excitation Thresholds," IEEE Transactions on Biomedical Engineering, vol. 39, No. 12, Dec. 1992, pp. 1244-1254.
Zhang et al., "Influence of Inter-Stimulus Interval of Spinal Cord Stimulation in Patients with Disorders of Consciousness: A Preliminary Functional Near-Infrared Spectroscopy Study," NeuroImage: Clinical, vol. 17, Sep. 23, 2017, 9 pages.
Thrasher et al., "Reducing Muscle Fatigue Due to Functional Electrical Stimulation Using Random Modulation of Stimulation Parameters," Artificial Organs, vol. 29, No. 6, Feb. 2005, pp. 453-458.
Slavin, "Spinal Stimulation for Pain: Future Applications," Neurotherapeutics, Apr. 3, 2014, pp. 535-541.
Redman et al., "Monosynaptic Stochastic Stimulation of Cat Spinal Motoneurons. II. Frequency Transfer characteristics of Tonically Discharging Motoneurons," Journal of Neurophysiology, vol. 31, No. 4, Jul. 1968, pp. 499-508.
Pinter et al., "Epidural Electrical Stimulation of Posterior Structures of the Human Lumboscral Cord: 3. Control of Spasticity," Spinal Cord, vol. 38, No. 9, Sep. 2000, pp. 524-531.
Redman et al., "Monosynaptic Stochastic Stimulation of Cat Soinal Motoneurons. I. Response of Motoneurons to Sustained Stimulation," vol. 31, No. 4, Jul. 1968, pp. 485-498.
Si et al., "Spinal Cord Stimulation Frequency Influences the Hemodynamic Response in Patients with Disorders of Consciousness," Neuroscience Bulletin, vol. 34, No. 4, Aug. 2018, pp. 659-667.
Martinez et al., "Stochastic Resonance in the Motor System: Effects of Noise on the Monosynaptic Reflex Pathway of the Cat Spinal Cord," Journal of Neurophysiology, vol. 97, No. 6, Apr. 11, 2007, pp. 4007-4016.
Manjarrez et al., "Internal Stochastic Resonance in the Coherence Between Spinal and Cortical Neoronal Ensembles in the Cat," Neuroscience Letters, vol. 326, Feb. 2002, pp. 93-96.
Chang et al., "Stochastic Versus Deterministic Variability in Simple Neuronal Circuits: 1. Monosynaptic Spinal Cord Reflexes," Biophysics Journal, vol. 67, Aug. 1994, pp. 671-683.
Dimitrijevic et al., "Habituation: Effects of Regular and Stochastic Stimulation," Journal of Neurology, Neurosurgery, and Psychiatry, vol. 35, No. 2, Apr. 1972, pp. 234-242.
Manjarrez et al., "Stochastic Resonance within the Somatosensory System: Effects of Noise on Evoked Field Potentials Elicited by Tactile Stimuli," The Journal of Neuroscience, vol. 23, No. 6, Mar. 15, 2003, pp. 1997-2001.
De Ridder et al., "Fundamentals of Burst Stimulation of the Spinal Cord and Brain," Chapter 14, Neuromodulation, Second Edition, Available Online Jan. 12, 2019, pp. 147-160.
Aksoz et al. "Effect of Stochastic Modulation of Inter-Pulse Interval During Stimulated Isokinetic Leg Extension," European Journal of Translational Myology, vol. 26, No. 3.
Bloodworth et al., "Comparison of Stochastic vs.Conventional Transcutaneous Electrical Stimulation for PainModulation in Patients withElectromyographically Documented Radiculopathy," American Journal of Physical and Medical Rehabilitation, vol. 83, No. 8, Aug. 2004, pp. 584-591.
Irazoqui et al., "System for Wireless Recording and Stimulating of Bioelectric Events," DARPA N66001-11-1-4029, Dec. 12, 2017, 12 pp.
U.S. Appl. No. 62/348,405, by Irazoqui et al., filed Jun. 10, 2016.
Seburn et al., "Miniature Wireless and Batteryless Device for Longitudinal Recording and Stimulating of Bioelectric Events in Small Animals," 45th Annual Meeting of the Society for Neuroscience, Oct. 17-21, 2015, 1 pp.
"St. Jude's Prodigy Neurostimulator with Burst Technology," Medgadget, Mar. 20, 2014, 4 pp.
Abejon et al., "Back pain coverage with spinal cord stimulation: A different treatment for each patient," International Neuromodulation Society. Jun. 10, 2015; 567, Abstract Only, 1 pp.
Abeloos, et al., "High density stimulation as an alternative to uncomfortable cervical tonic spinal cord stimulation: case report," International Neuromodulation Society 12th World Congress, Jun. 11-15, 2015, Abstract Only, 1 pp.
Breel, et al., "High Density Stimulation: A novel programming paradigm for the treatment of chronic pain," International Neuromodulation Society (INS) 12th World Congress; Jun. 9, 2015, Abstract Only, 1 pp.
Cuellar MD et al., "Effect of high-frequency alternating current on spinal afferent nociceptive transmission," Neuromodulation: Technology at the Neural Interface; Jul.-Aug. 2013;16(4): pp. 318-327.
Cui, et al., "Effect of spinal cord stimulation on tactile hypersensitivity in mononeuropathic rats is potentiated by simultaneous GABA(B) and adenosine receptor activation," Neuroscience Letters 247: Apr. 1998; pp. 183-186.
Cui et al., "Spinal cord stimulation attenuates augmented dorsal horn release of excitatory amino acids in mononeuropathy via a GABAergic mechanism," Pain 73, Oct. 1997, pp. 87-95.
De Ridder, et al., "Burst spinal cord stimulation for limb and back pain," World neurosurgery, Nov. 2013; 80(5):642-649 e641.
De Ridder, et al., "Burst spinal cord stimulation: toward paresthesia-free pain suppression," Neurosurgery. May 2010; 66(5): 986-990.
Downey, "Asynchronous Neuromuscular Electrical Stimulation," University of Florida, 2015, accessed on Jul. 18, 2016, 107 pp.
Duyvendak, MD, et al., "High density stimulation: a novel programming paradigm for the treatment of chronic back and leg pain," Abstracts, International Neuromodulation Society 12th World Congress: Jun. 11-15, 2015, 1 pp.
Gao et al., "Effects of spinal cord stimulation with "standard clinical" and higher frequencies on peripheral blood flow in rats," Brain Res. Feb. 8 2010;1313: pp. 53-61.
Grider, et al., "High Frequency (1000 Hz) Stimulation Using Commercially Available Implantable Pulse Generator," North American Neuromodulation Society. Dec. 2013, Abstract Only, 2 pp.
Guan et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.
Guan et al., "Spinal Cord Stimulation: Neurophysiological and Neurochemical Mechanisms of Action" Curr Pain Headache Rep DOI 10,1007s11916-014-0260-4, Mar. 2012, pp. 217-225.
Holsheimer, "Computer modelling of spinal cord stimulation and its contribution to therapeutic efficacy," Spinal Cord Aug. 1998, 36: pp. 531-540.
Hunt SP, Mantyh PW. The molecular dynamics of pain control. Nat Rev Neurosci. Feb. 2001;2(2):83-91.
Kemler, et al., "Spinal cord stimulation in patients with chronic reflex sympathetic dystrophy," N Engl J Med, Aug. 31, 2000; 343(9):618-624.
Kilgore, PhD, et al., "Reversible Nerve Conduction Block Using Kilohertz Frequency Alternating Current," Neuromodulation. Aug. 2013, pp. 242-255.
Kumar, et al., "Spinal cord stimulation versus conventional medical management for neuropathic pain: a multicentre randomised controlled trial in patients with failed back surgery syndrome," Pain Jul. 2007; 132(1-2): 179-188.
Likar et al., "High density spinal cord stimulation: a multi-center experience," Abstracts, International Neuromodulation Society 12th World Congress; Jun. 11-15, 2015, 1 pp.
Sweet et al., "High Frequency vs. Burst Stimulation Patterns for Dorsal Column Stimulation: The Importance of Charge," American Association of Neurological Surgeons, Abstract, Apr. 4, 2014, 2 pp.
Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.
North M.D. et al., "Spinal cord stimulation versus repeated lumbosacral spine surgery for chronic pain: a randomized, controlled trial," Neurosurgery, Jan. 2005; 56(1): 98-106; discussion 106-107.
North, et al., "Clinical outcomes of 1 kHz subperception spinal cord stimulation (SCS): Results of a prospective randomized controlled crossover trial," Abstracts, International Neuromodulation Society, Jun. 2015, 1 pp.

(56) References Cited

OTHER PUBLICATIONS

Ranck Jr., et al., "Which elements are excited in electrical stimulation of mammalian central nervous system: a review," Brain Res. Nov. 21, 1975; 98(3): pp. 417-440.
Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the affective U.S. filing date of the present application, and any foreign priority date that the particular month of publication is not in issue.
Sato, et al., "Spinal cord stimulation reduces hypersensitivity through activation of opioid receptors in a frequency-lependent manner," Eur J Pain. Apr. 17, 2012 (4): pp. 551-561.
Song, et al., "Efficacy of kilohertz-frequency and conventional spinal cord stimulation in rat models of different pain conditions," Neuromodulation Jan. 2014; 17(3): pp. 226-234.
Schu et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.
Shechter et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the affective U.S. filing date of the present application, and any foreign priority date that the particular month of publication is not in issue.
Maeda, et al., "Increased c-fos immunoreactivity in the spinal cord and brain following spinal cord stimulation is frequency-dependent," Brain Res. Mar. 9, 2009;1259: pp. 40-50.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith, et al., "Successful use of high-frequency spinal cord stimulation following traditional treatment failure," Stereotact Funct Neurosurg. Apr. 2015; 93(3): pp. 190-193.
Wille, MD, et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.

Maggi, et al., "Effect of urethane anesthesia on the micturition reflex in capsaicin-treated rats." Journal of the Autonomic Nervous System, Jan. 1990, 30(3): 247-251.
Walter, et al., "Inhibiting the hyperreflexic bladder with electrical stimulation in a spinal animal model." Neurourology and Urodynamics, 1993, 12:241-253. Applicant points out in accordance with MPEP 609.04(a) that the 1993 year of publication is sufficiently earlier than the effective U.S. filing date of the present application, and any foreign priority date that the particular month of publication is not in issue.
Hubscher, et al., "Convergence and cross talk in urogenital neural circuitries," J. Neurophysiol 110: 1997-2005, first published Aug. 7, 2013, 9 pp.
Snellings et al., "Effects of stimulation site and stimulation parameters on baldder inhibition by electrical nerve stimulation," BJU International, published Aug. 9, 2011, pp. 136-143.
Woock, et al., "Activation and inhibition of the micturition reflex by penile afferents in the cat," Am J. Physiol Regul Intergre Comp Physiol, published Apr. 23, 2008, pp. R1880-R1889.
U.S. Appl. No. 15/623,141, by Nathan A. Torgerson, filed Jun. 14, 2017.
Response to Office Action dated Jul. 3, 2018, from U.S. Appl. No. 15/967,329, filed Oct. 3, 2018, 2 pp.
Office Action from U.S. Appl. No. 15/967,329, dated Jul. 3, 2018, 6 pp.
U.S. Appl. No. 15/946,971, filed Apr. 6, 2018, by Brink et al.
Bhadra et al., "High frequency electrical conduction block of the pudendal nerve," Journal of Neural Eng., IOP Publishing LTD, published Jun. 3, 2006,14 pp.
Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.
Walter et al., "Inhibiting the hyperreflexic bladder with electrical stimulation in a spinal animal model." Neurourology and Urodynamics, 1993, 12:241-253. Applicant points out in accordance with MPEP 609.04(a) that the 1993 year of publication is sufficiently earlier than the effective U.S. filing date of the present application, and any foreign priority late that the particular month of publication is not in issue.
International Preliminary Report on Patentability from International Application No. PCT/US2017/064925, dated Jun. 11, 2019, 7 pp.
Prosecution History from U.S. Appl. No. 14/946,431, dated Mar. 22, 2017 through Dec. 22, 2017, 36 pp.
Examination Report from counterpart European Application No. 17822852.4, dated Jul. 13, 2020, 5 pp.

\* cited by examiner

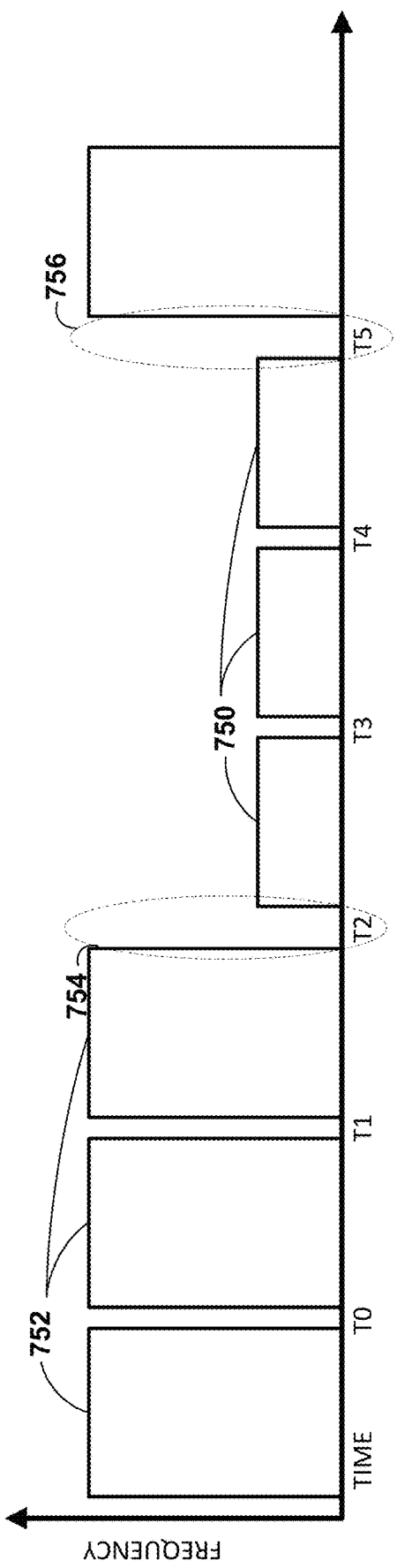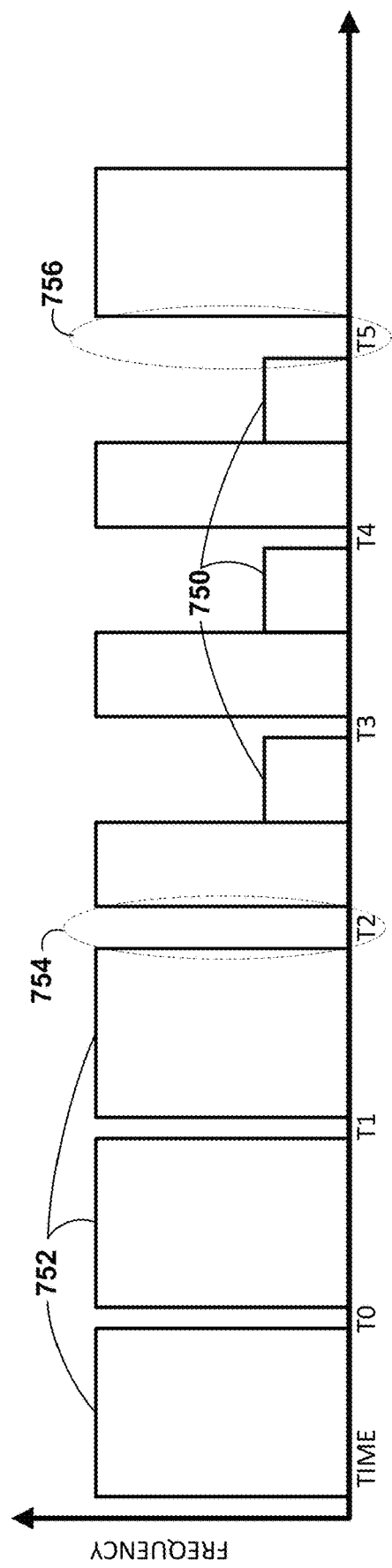

HIGH FREQUENCY NEUROSTIMULATION FOR PELVIC SYMPTOM CONTROL

This application claims the benefit of U.S. Provisional Application No. 62/430,498 by Brink et al., entitled "HIGH FREQUENCY NEUROSTIMULATION FOR PELVIC SYMPTOM CONTROL" and filed on Dec. 6, 2016. The entire content of Application No. 62/430,498 is incorporated herein by reference.

TECHNICAL FIELD

This disclosure generally relates to electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

In general, the disclosure describes techniques for delivering high frequency neurostimulation (e.g., electrical stimulation comprising a frequency greater than or equal to about 1,000 Hertz) to control one or more pelvic disorders of a human patient, such as urinary bladder function disorders (including urgency, incontinence, or retention), pelvic pain, bowel dysfunction, or sexual dysfunction. In one example of the techniques disclosed herein, a medical system including an implantable medical device (IMD) delivers high frequency electrical stimulation to a human patient to increase bladder capacity and decrease urinary frequency and incontinence. In some examples, the medical system interleaves combinations of high frequency signals and low frequency signals to control pelvic dysfunctions or to provide different types of therapy for different patient activities. In yet further examples, the medical system, based on temporal and spatial monitoring of the patient, delivers high frequency electrical stimulation to a patient at specific times and locations.

In one example, this disclosure describes a method for delivering electrical stimulation with a medical device configured to be at least partially implanted in a patient, the method including: identifying, by the medical device, an indication to inhibit bladder activity; generating, by the medical device and in response to identifying the indication, electrical stimulation therapy including first electrical stimulation pulses including a first frequency greater than or equal to about 500 Hertz and less than or equal to about 5,000 Hertz; and delivering, by the medical device, the electrical stimulation therapy to a target nerve selected from a group consisting of: a sacral nerve, a pelvic nerve, a tibial nerve, and a pudendal nerve of the patient.

In another example, this disclosure describes a medical system including a medical device configured to be at least partially implanted in a patient, the medical device including: a lead including one or more electrodes and configured for placement near a target nerve selected from a group consisting of: a sacral nerve, a pelvic nerve, a tibial nerve, and a pudendal nerve of the patient; electrical stimulation generation circuitry configured to generate electrical stimulation therapy including first electrical stimulation pulses including a first frequency greater than or equal to about 500 Hertz and less than or equal to about 5,000 Hertz; and processing circuitry configured to: identify an indication to inhibit bladder activity; and control the electrical stimulation generation circuitry to deliver the electrical stimulation therapy to the target nerve via the one or more electrodes.

In another example, this disclosure describes a medical device configured to be at least partially implanted in a patient, the medical device including: means for identifying an indication to inhibit bladder activity; means for generating, in response to identifying the indication, electrical stimulation therapy including first electrical stimulation pulses including a first frequency greater than or equal to about 500 Hertz and less than or equal to about 5,000 Hertz; and means for delivering the electrical stimulation therapy to a target nerve selected from a group consisting of: a sacral nerve, a pelvic nerve, a tibial nerve, and a pudendal nerve of the patient.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 7A-7D are timing diagrams depicting example electrical stimulation therapies that the IMD of FIG. 1 delivers to the patient.

DETAILED DESCRIPTION

Figure 1:
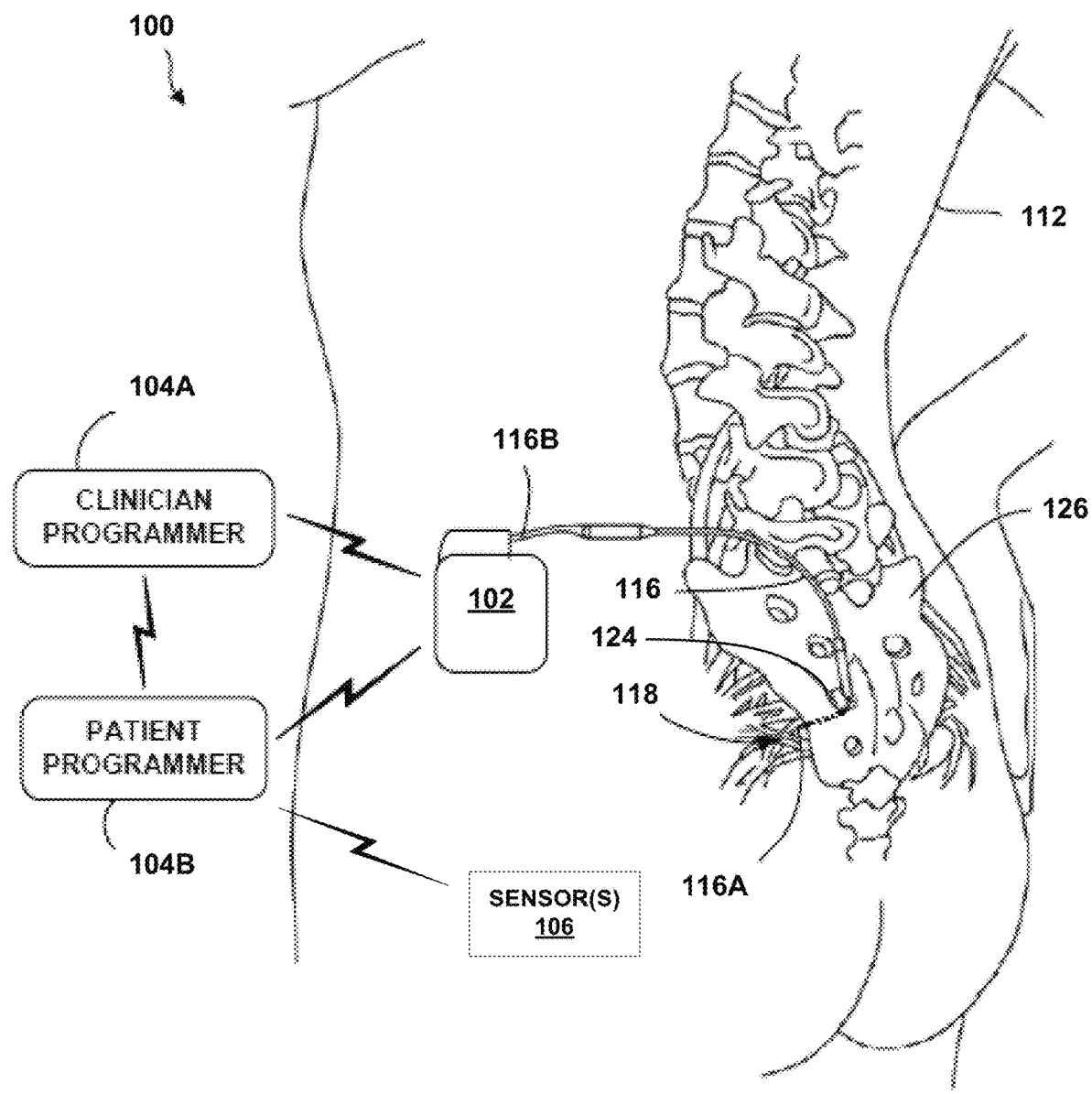
FIG. 1 is a conceptual diagram illustrating an example system that includes a medical device programmer and an implantable medical device (IMD) configured to deliver higher frequency electrical stimulation therapy to a patient.

Previous animal studies have investigated the feasibility of high frequency electrical stimulation (e.g., electrical stimulation comprising a frequency of about 1,000 Hertz) delivered to control one or more pelvic disorders in animal subjects. Such studies demonstrated that high frequency electrical stimulation caused significant side effects in anesthetized animal subjects, such as leg flexion and secondary bladder contractions in anesthetized felines. These animal studies suggested that such high frequency electrical stimulation was not only less effective than conventional low frequency electrical stimulation (e.g., electrical stimulation comprising a frequency equal to or less than 50 Hertz) in providing therapy for the one or more pelvic disorders, but additionally suggested that such high frequency electrical stimulation would not be a viable therapy for human patients, e.g., due to the significant side effects and reduced efficacy relative to lower frequency stimulation.

Contrary to the results of these animal studies, it has been discovered that delivering high frequency electrical stimulation comprising a frequency equal to or greater than 1,000 Hertz may provide therapeutic advantages when controlling symptoms of the one or more pelvic disorders of a human patient, relative to conventional low frequency electrical stimulation, e.g., improved inhibition of voiding and resulting increase in bladder capacity. Furthermore, it has been discovered that such high frequency electrical stimulation did not induce the substantial side effects observed in the prior animal studies. The discovery that high frequency electrical stimulation has improved therapeutic results and does not induce substantial side effects was unexpected and surprising in light of the animal studies that demonstrated that similar high frequency electrical stimulation was less effective and caused negative side effects in animal patients. Without being limited by theory, it is believed that at least some of the surprising results can be attributed to the prior studies using anesthetization, and in at least one instance, to spinal cord injuries of the subject animals. New data suggests that fully conscious animals, and therefore potentially human patients, may not demonstrate the side effects that previous studies have observed in animals with spinal cord injuries.

A further unexpected and surprising result was the discovery that a certain frequency range of high frequency electrical stimulation, a range of about 1,000 Hertz to 5,000 Hertz, provided improved therapeutic results relative to frequencies outside of the frequency range. Accordingly, techniques making use of these unexpected and surprising results are disclosed herein for delivering high frequency electrical stimulation to a human patient to provide therapeutic control one or more pelvic disorders of the human patient. In some examples, the high frequency electrical stimulation is delivered to at least one of a sacral nerve, dorsal nerve of the penis, dorsal nerve of the clitoris, or a pudendal nerve of the human patient.

FIG. 1 is a schematic perspective view of an example electrical stimulation system 100 that is configured to provide therapy for a pelvic symptom or pelvic floor disorder of patient 112. Electrical stimulation system 100 is configured to deliver electrical stimulation to a target tissue, such as one or more nerves in the pelvic floor. In some examples, system 100 may generate stimulation in response to a sensed signal or at predetermined times. In other examples, system 100 may receive input from a user, e.g., patient 112, indicating that patient 112 is attempting to contract one or more pelvic floor muscles and deliver electrical stimulation to a target tissue site proximate a nerve of patient 112 based on the input. For example, the electrical stimulation may be configured to induce or suppress a contraction in the pelvic floor muscles. The nerve can be a nerve that influences the behavior of pelvic floor muscles of patient 112, such as a sacral nerve, a pudendal nerve, pelvic nerve, tibial nerve, dorsal nerve of the penis, dorsal nerve of the clitoris, or another branch of the sacral, pudendal, or pelvic nerves. While the sacral and pudendal nerves are primarily referred to throughout the disclosure, in other examples, therapy system 100, as well as the other systems, can include delivery of stimulation to tissue sites proximate to other nerves in addition to or instead of the sacral or pudendal nerves. Moreover, reference to the sacral and pudendal nerves may include branches of the sacral and pudendal nerves that may also influence the behavior of pelvic floor muscles of patient 112. In further examples, therapy system 100 includes delivery of stimulation to tissue sites proximate to lumbar or thoracic spinal nerves or their branches, such as chain ganglia, sympathetic or parasympathetic ganglia, S1-S5, pelvic nerve, a dorsal nerve of a clitoris or a penis, an inferior rectal nerve, a peroneal nerve, a sciatic nerve, a tibial nerve, or other nerve targets. It has been recognized that there are many similarities in the therapeutic effects of electrical stimulation between each of the sacral nerve, tibial nerve, dorsal nerve of the penis, dorsal nerve of the clitoris, or a pudendal nerve. Accordingly, various the electrical stimulations discussed herein are applicable to stimulation applied to each such nerve. For ease of discussion, various embodiments are discussed in connection with stimulation applied proximate to one or both of the sacral nerve and the pudendal nerve. It is understood that the concepts discussed in these embodiments can also be applied to the tibial nerve, dorsal nerve of the penis, or dorsal nerve of the clitoris.

Although system 100 may deliver electrical stimulation to modulate muscle activity, such as by modulating motoneurons, to treat incontinence and/or overactive bladder (e.g., contract or relax a sphincter or inhibit bladder contractions), system 100 may also deliver stimulation configured to treat pain or other symptoms, such as by modulating the activity of sensory or afferent nerve fibers. In some examples, system 100 may be configured to deliver stimulation to nerves that innervate the bladder, the rectum, or sexual organs in order to treat a variety of symptoms. In other examples, system 100 may be configured to provide spinal cord stimulation, peripheral nerve stimulation, occipital nerve stimulation, gastric stimulation, or any other therapy configured to modulate organ or muscle activity and/or treat pain.

Electrical stimulation system 100 includes implantable medical device (IMD) 102, which is coupled to lead 116, for delivering electrical stimulation to target tissue site 118 of patient 112. In addition, electrical stimulation system 100 includes clinician programmer 104A and patient programmer 104B (collectively, "programmers 104") for integrating a clinician and patient 112, respectively, into electrical stimulation system 100. In some examples, only a single external programmer may be used to communicate with IMD 102.

IMD 102 may provide electrical stimulation therapy to target tissue site 118 of patient 112 by generating a programmable electrical stimulation signal (e.g., in the form of electrical pulses, signals, or waveforms) and delivering the electrical stimulation signal to target tissue site 118 via lead 116. In some examples, IMD 102 is located proximate a sacral nerve, tibial nerve, dorsal nerve of the penis, dorsal nerve of the clitoris, or a pudendal nerve of patient 112. In some examples, lead 116 includes one or more stimulation electrodes, disposed on distal end 116A of lead 116 and implanted proximate to target tissue site 118 such that the electrical stimulation is delivered from IMD 102 to target tissue site 118 via the stimulation electrodes.

In some examples described herein, target tissue site 118 includes at least one of a sacral nerve of patient 112, a pudendal nerve of patient 112 (or a tissue site proximate the sacral or pudendal nerve, wherein delivery of electrical stimulation to the tissue site captures the nerve), or a pelvic nerve of patient 112. The sacral and pudendal nerves of patient 112 may be involved in inducing or inhibiting a contraction in one or more muscles of the pelvic floor of patient 112. As a result, electrical stimulation of the sacral and/or pudendal nerves of patient 112 may be useful in treating the pelvic floor disorder of patient 112.

In general, the sacral nerves include five sacral nerves that emerge bilaterally from the sacrum. In some examples, the sacral vertebrae (S1-S5) may be used to number the sacral nerves. The sacral nerves contribute to the sacral plexus (a network of intersecting nerves that innervates the posterior thigh, part of the lower leg, the foot, and part of the pelvis as well as transmits sensory information from those areas to the central nervous system) and the coccygeal plexus (a network of intersecting nerves near the coccyx bone, e.g., the tailbone, that innervates the skin of the coccyx bone and around the anus). In general, the pudendal nerve is a somatic nerve in the pelvic region, which is a large branch of the sacral plexus. The pudendal nerve innervates the external genitalia, the urinary sphincters, and the anal sphincters.

As illustrated in FIG. 1, distal end 116A of lead 116 is implanted proximate to target tissue site 118 (e.g., proximate to a target nerve). In the example shown in FIG. 1, target tissue site 118 is proximate the S3 sacral nerve of patient 112. In this example, in order to implant distal end 116A of lead 116 proximate to the S3 sacral nerve, lead 116 may be introduced into the S3 sacral foramen 124 of sacrum 126 to access the S3 sacral nerve. For some patients, stimulation of the S3 sacral nerve may be effective in treating a pelvic floor disorder of the patient. In other examples, distal end 116A may be implanted proximate to a different target tissue site, such as a target tissue site proximate to a different sacral nerve or a pudendal or pelvic nerve of patient 112 to treat the pelvic floor disorder of patient 112.

Although FIG. 1 illustrates one lead 116, in some examples, IMD 102 may be coupled to two or more leads, e.g., to facilitate bilateral or multi-lateral stimulation. In some examples, lead 116 may also carry one or more sense electrodes via which IMD 102 can sense one or more physiological parameters (e.g., nerve signals, EMG, and the like) of patient 112, in addition to the one or more stimulation electrodes carried by lead 116. In some examples, lead 116 includes a lead body, and proximal end 116B of lead 116 may be electrically coupled to IMD 102 via one or more conductors extending substantially through the lead body between the one or more stimulation electrodes carried by lead 116 and IMD 102.

In the example shown in FIG. 1, lead 116 is cylindrical. One or more electrodes of lead 116 may be ring electrodes, segmented electrodes, or partial ring electrodes. Segmented and partial ring electrodes each extend along an arc less than 360 degrees (e.g., 90-120 degrees) around the outer perimeter of the lead 116. In some examples, segmented electrodes may be useful for targeting different fibers of the same or different nerves to generate different physiological effects. The electrodes of lead 116 may be used for delivering relatively high frequency stimulation (e.g., greater than about 100 Hertz) and relatively low frequency stimulation (e.g., less than about 50 Hertz) to induce or suppress responses in pelvic muscles or nerves of patient 112. In some examples, lead 116 may be, at least in part, paddle-shaped (e.g., a "paddle" lead).

In some examples, one or more of the electrodes of lead 116 may be cuff electrodes that are configured to extend at least partially around a nerve (e.g., extend axially around an outer surface of a nerve). In some cases, delivering stimulation via one or more cuff electrodes and/or segmented electrodes may help achieve a more uniform electrical field or activation field distribution relative to the nerve in some examples, which may help minimize discomfort to patient 112 that results from the delivery of electrical stimulation. An electrical field represents the areas of a patient anatomical region that are covered by an electrical field during delivery of electrical stimulation to tissue within patient 112. The electrical field may define the volume of tissue that is affected when the electrodes of lead 116 are activated. An activation field represents the neurons that will be activated by the electrical field in the neural tissue proximate to the activated electrodes.

The illustrated numbers and configurations of lead 116 and electrodes carried by lead 116 are merely one example. Different configurations, e.g., different quantities and/or positions of leads and electrodes, are possible. For example, in other examples, IMD 102 may be coupled to additional leads or lead segments having one or more electrodes positioned at different locations in the pelvic region of patient 112.

IMD 102 may be surgically implanted in patient 112 at any suitable location within patient 112, such as within in an abdomen of patient 112. In some examples, the implantation site may be a subcutaneous location in the side of the lower abdomen or the side of the lower back or upper buttocks. IMD 102 has a biocompatible outer housing, which may be formed from titanium, stainless steel, a liquid crystal polymer, or the like. In some examples, electrical conductors disposed within the lead body of lead 116 electrically connect electrodes to electrical stimulation delivery circuitry within IMD 102. In other examples, therapy system 100 may include a leadless electrical stimulator, such as a microstimulator (e.g., a capsule shaped microstimulator), where the leadless electrical stimulator delivers electrical stimulation to target tissue site 118, and, in some examples, senses one or more physiological parameters of patient 112, via electrodes on an outer surface of the electrical stimulator housing and without the aid of electrodes of a lead that extends from the electrical stimulator housing.

IMD 102 may deliver electrical stimulation to manage a pelvic symptom of patient 112 (e.g., functional electrical stimulation for a voiding disorder or urinary incontinence). In these examples, IMD 102 may deliver electrical stimulation configured to contract a muscle (e.g., the urinary sphincter) to help suppress or prevent involuntary voiding events in order to manage, e.g., urinary incontinence or fecal incontinence of patient 112. In addition, or alternatively, IMD 102 may deliver electrical stimulation configured to relax a bladder (e.g., inhibit bladder contractions) of patient 112 to help prevent urgency. In other examples, electrical stimulation may be provided to train and/or strengthen pelvic floor muscles. In still further examples, IMD 102 may deliver electrical stimulation configured to control pelvic dysfunctions such as overactive bladder (OAB) disease, pelvic pain, sexual dysfunction, and other visceral or pelvic disorders.

In the example illustrated in FIG. 1, system 100 includes clinician programmer 104A and patient programmer 104B. In some examples, one or both programmers 104A and 104B may be wearable communication devices integrated into a key fob or a wrist watch. In other examples, one or both programmers 104A and 104B may be handheld computing devices, computer workstations, or networked computing devices. Programmers 104 may include respective user interfaces that receive input from a user (e.g., a clinician or patient 112, respectively). The user interfaces may include components for interaction with a user, such as a keypad and a display. In some examples, the display may be a cathode ray tube (CRT) display, a liquid crystal display (LCD) or light emitting diode (LED) display and the keypad may take the form of an alphanumeric keypad, or a reduced set of keys associated with particular functions. Programmers 104 can, additionally or alternatively, include a peripheral pointing device, e.g., a mouse, via which a user may interact with the user interface. In some examples, the displays may include a touch screen display, and a user may interact with programmers 104 via the touch screens of the displays. In some examples, the user may also interact with programmers 104 and/or IMD 102 remotely via a networked computing device.

Clinician programmer 104A facilitates interaction of a clinician with one or more components of system 100. In some examples, the clinician, (e.g., physician, technician, surgeon, electrophysiologist, or other clinician) may interact with clinician programmer 104A to communicate with IMD 102. For example, the clinician may retrieve physiological or diagnostic information from IMD 102 via clinician programmer 104A. As another example, the clinician may interact with programmer 104A to program IMD 102, e.g., select values of respective stimulation parameters that define electrical stimulation generated and delivered by IMD 102, select other operational parameters of IMD 102, etc. As another example, the clinician may use programmer 104A to retrieve information from IMD 102 regarding the performance or integrity of IMD 102 or other components of system 100, such as lead 116 or a power source of IMD 102. In some examples, this information may be presented to the clinician as an alert if a system condition that may affect the efficacy of therapy is detected.

In some examples, a clinician may use clinician programmer 104A to create stimulation programs for electrical stimulation (generated and delivered by IMD 102) of the nerves configured to induce or suppress a contraction in one or more pelvic floor muscles of the patient. The stimulation programs may describe a plurality of different electrical stimulus parameter sets for delivering electrical stimulus therapy to patient 112. The electrical stimulus parameter sets may, in some examples, specify the number or time duration of one or more stimulation pulses, the number of times the electrical stimulus is delivered within a particular period of time (e.g., daily), particular times of day at which the electrical stimulus is delivered, and other parameters relating to the delivery of stimulation to patient 112. In some examples, the clinician programmer 104A transmits the stimulation programs to IMD 102 for storage in a memory of IMD 102.

Patient programmer 104B facilitates interaction of patient 112 with one or more components of system 100. In some examples, patient 112 may interact with patient programmer 104B to control IMD 102 to deliver electrical stimulation, to manually abort the delivery of electrical stimulation by IMD 102, or to inhibit the delivery of electrical stimulation by IMD 102. Patient 112 may, for example, use a keypad or touch screen of programmer 104B to cause IMD 102 to deliver electrical stimulation, e.g., to activate one or more stimulation programs.

IMD 102, clinician programmer 104A, and patient programmer 104B may communicate via wireless communication using any techniques known in the art. Examples of communication techniques may include, for example, low frequency or radiofrequency (RF) telemetry. Other techniques are also contemplated. In some examples, programmer 104A and/or programmer 104B may include a programming head that may be placed proximate to the body of the patient near the IMD 102 implant site in order to improve the quality or security of communication between IMD 102 and programmers 104.

According to the techniques of the disclosure, IMD 102 delivers electrical stimulation therapy to a target tissue site of patient 112 to provide therapy for one or more pelvic symptoms of patient 112. IMD 102 delivers the electrical stimulation according to at least one therapy program. In some examples, IMD 102 delivers electrical stimulation according to an electrical stimulation therapy program comprising a high frequency (e.g., a frequency greater than about 100 Hertz). In some examples, the high frequency is greater than about 1,000 Hertz and less than about 5,000 Hertz. In other examples, the high frequency is about 1,000 Hertz. Such an electrical stimulation therapy may suppress one or more symptoms of the pelvic symptoms of patient 112, while reducing or preventing side effects of the electrical stimulation therapy, such as paresthesia. Further, electrical stimulation therapy delivered at such a frequency range may have greater efficacy than electrical stimulation therapy delivered at frequencies lower than 1,000 Hertz or greater than 5,000 Hertz. As discussed earlier, certain techniques of the disclosure make use of the unexpected and surprising discovery that electrical stimulation delivered according to an electrical stimulation therapy program comprising the high frequency does not induce substantial side effects in patients and can provide improvements to therapeutic results in patients relative to electrical stimulation delivered according to a conventional electrical stimulation therapy program comprising a low frequency.

In some examples, delivering the electrical stimulation therapy at the high frequency may suppress one or more symptoms of the pelvic symptoms without inducing substantial side effects in patient 112. As described herein, some examples of substantial side effects include a perception of paresthesia or pain by patient 112, or an observable muscle response in patient 112 (e.g., muscle twitching). By using the techniques of the disclosure, IMD 102 may suppress the one or more symptoms of the pelvic symptoms without inducing such substantial side effects in patient 112.

In other examples, IMD 102 interleaves a first electrical stimulation therapy program having a high frequency and a second electrical stimulation therapy program having a low frequency (e.g., a frequency less than about 50 Hertz), and delivers electrical stimulation to patient 112 according to the interleaved first and second electrical stimulation therapy programs. Such a combined electrical stimulation therapy may suppress one or more symptoms of the pelvic symptoms of patient 112, while reducing or preventing side effects of the electrical stimulation therapy, such as paresthesia.

In some examples, high frequency (e.g., greater than 100 Hertz) neuromodulation is delivered to a pudendal nerve of the patient. The high frequency stimulation of the pudendal nerve may block urethra contraction and inhibit voiding in cats. Such high frequency stimulation could be used to provide therapy to patients with bladder sphincter dyssynergia. Such high frequency stimulation may enhance effectiveness in reducing sensations of a patient, such as urgency, pain, and leaks so as to promote increases in bladder capacity or otherwise assist with the storage of urine. Further, such high frequency stimulation may require lower stimulation amplitude to achieve therapeutic effects than lower frequency stimulation as well as may reduce unwanted sensations associated to stimulation, such as paresthesia or unwanted and/or unpleasant stimulation.

In some examples of the techniques herein, system 100 includes one or more sensors 106 configured to detect one or more parameters related to the disease of patient 112 or the state of patient 112 generally. In some examples, sensors 106 may be accelerometers, magnetometers, pressure sensors, bending sensors, sensors configured to detect a posture of the patient, or sensors configured to detect a respiratory function of patient. In further examples, sensors 106 may be configured to detect an evoked compound action potential (ECAP) of a tissue of patient 112, such as a nerve tissue or muscle tissue of patient 112. For example, sensors 106 may be configured to detect the presence or absence of at least one type of urinary activity of patient 112, such as a bladder voiding event or a bladder contraction event. In further examples, sensors 106 are configured to detect one or more environmental parameters of patient 112. For example, sensors 106 may be configured to detect the time of day, a spatial positioning of patient 112, or a posture of patient 112. Such sensors 106 may include accelerometers, magnetometers, chronometers, pedometers, GPS sensors, and the like. In yet further examples, sensors 106 are configured to detect one or more biomarkers of patient 112. Such sensors 106 may be chemical or biochemical sensors or sensors configured to sense a particular component, such as a cell, molecule, gene, gene product, enzyme, hormone, chromosome, or cell, within a tissue or blood of patient 112.

Using such information from sensors 106, system 100 may more accurately predict urinary activity of patient 112, and therefore provide electrical stimulation therapy that is more precisely configured for the dynamic needs of patient 112 than other devices. As one example, IMD 102 delivers electrical stimulation to patient 112. Upon detecting that patient 112 has, for example, entered his bathroom, that the time is in the evening or night, that patient 112 is standing, that patient 112 has commenced a voiding event, or any combination of one or more of the foregoing, IMD 102 may determine that there is a heightened probability that patient 112 requires adjustment of the electrical stimulation therapy to assist patient 112 with the urinary activity (e.g., to cease bladder retention therapy when voiding is required). In response to determining that there is a heightened probability that patient 112 requires adjustment of the electrical stimulation therapy to assist patient 112 with the urinary activity, IMD 102 adjusts one or more parameters defining the electrical stimulation therapy to provide context-aware electrical stimulation therapy to patient 112.

In some examples, system 100, via electrodes of IMD 102, determines the effectiveness of the electrical stimulation therapy delivered to patient 112. For example, the electrodes may sense an ECAP of a tissue of patient 112, and based on the sensed ECAP, determine the efficacy of the electrical stimulation. In some examples, the electrodes that sense ECAP are the same electrodes as the electrodes that deliver electrical stimulation to patient 112, while in some examples, the electrodes that sense ECAP are other electrodes on the stimulation lead 116, electrodes on a lead separate from stimulation lead 116, or electrodes of a separate sensing device.

In some examples, IMD 102, during normal operation, continuously delivers electrical stimulation therapy according to an electrical stimulation therapy program having a high frequency (e.g. a frequency greater than about 100 Hertz) to provide bladder control therapy to patient 112. In some examples, the high frequency is greater than about 1,000 Hertz and less than about 5,000 Hertz. Such an electrical stimulation therapy may suppress one or more symptoms of the pelvic symptoms of patient 112, while reducing or preventing side effects of the electrical stimulation therapy, such as paresthesia. Further, electrical stimulation therapy delivered at such a frequency range may have greater efficacy than electrical stimulation therapy delivered at frequencies lower than 1,000 Hertz or greater than 5,000 Hertz. As discussed earlier, the techniques of the disclosure make use of the unexpected and surprising discovery that electrical stimulation delivered according to an electrical stimulation therapy program comprising the high frequency does not induce substantial side effects in patients and is can provide improved therapeutic effects for patients relative to electrical stimulation delivered according to a conventional electrical stimulation therapy program comprising a low frequency.

In other examples, IMD 102 interleaves the electrical stimulation therapy program having the high frequency and an electrical stimulation therapy program having a low frequency (e.g., a frequency less than about 50 Hertz), and delivers electrical stimulation therapy according to the interleaved electrical stimulation therapy programs to provide bladder control therapy to patient 112. In some examples, IMD 102 delivers the electrical stimulation therapy according to a duty cycle having periods of delivery of electrical stimulation pulses interleaved with periods of non-delivery of electrical stimulation pulses. In other examples, IMD 102 delivers continuous electrical stimulation therapy comprising a primary frequency component.

In some examples, in response to external input, IMD 102 may adjust one or more parameters defining the electrical stimulation therapy. Such external input may include a signal from sensors 106 indicating urinary activity, a time of day, a posture of patient 112, motion of patient 112, or a spatial positioning of patient 112. For example, in response to the external input, IMD 102 may suspend delivery of the electrical stimulation therapy according to an electrical stimulation therapy program having a high frequency. In other examples, IMD 102 adjusts one or more parameters defining the electrical stimulation therapy slightly before the urinary activity commences. In still further examples, IMD 102 adjusts one or more parameters defining the electrical stimulation therapy slightly after the urinary activity commences.

As another example, IMD 102, during normal operation, continuously delivers electrical stimulation therapy according to an electrical stimulation therapy program having a high frequency (e.g. a frequency greater than about 100 Hertz). In some examples, IMD 102 delivers the electrical stimulation therapy according to a duty cycle having periods of delivery of electrical stimulation pulses interleaved with periods of non-delivery of electrical stimulation pulses. In other examples, IMD 102 delivers continuous electrical stimulation therapy comprising a primary frequency component. In response to external input, IMD 102 may adjust one or more parameters defining the electrical stimulation therapy. Such external input may include a signal from sensors 106 indicating urinary activity, a time of day, a posture of patient 112, motion of patient 112, or a spatial positioning of patient 112. For example, in response to the external input, IMD 102 may suspend delivery of the electrical stimulation therapy according to an electrical stimulation therapy program having the high frequency, and begin delivery of electrical stimulation therapy according to an electrical stimulation therapy program having a low frequency (e.g. a frequency less than about 50 Hertz). In other examples, in response to the external input, IMD 102 interleaves an electrical stimulation therapy program having the high frequency and an electrical stimulation therapy program having the low frequency, and delivers electrical stimulation therapy according to the interleaved electrical stimulation therapy programs. In yet further examples, in response to the external input, IMD 102 interleaves an electrical stimulation therapy program having the high frequency and an electrical stimulation therapy program having a low frequency and a gradually increasing amplitude (e.g., a voltage amplitude or a current amplitude), and delivers electrical stimulation therapy according to the interleaved electrical stimulation therapy programs. In other examples, IMD 102 adjusts one or more parameters defining the electrical stimulation therapy slightly before the urinary activity commences. In still further examples, IMD 102 adjusts one or more parameters defining the electrical stimulation therapy slightly after the urinary activity commences.

In some examples, in response to detecting that the urinary activity has ceased, IMD 102 discontinues electrical stimulation therapy according to the electrical stimulation therapy program having the low frequency and resumes normal electrical stimulation therapy (e.g., electrical stimulation therapy according to the electrical stimulation therapy program having the high frequency). In other examples, IMD 102 discontinues electrical stimulation therapy according to the electrical stimulation therapy program having the low frequency after a predetermined amount of time. Such a predetermined amount of time may allow the patient to complete a bladder or fecal voiding event before resuming the normal electrical stimulation therapy.

In additional examples, IMD 102 may control delivery of electrical stimulation therapy based on feedback received from patient 112. For example, patient 112 may provide feedback via external programmer 104B, indicating that a urinary activity of patient 112 has commenced or is about to commence. In response to such patient feedback, IMD 102 may adjust one or more parameters of the electrical stimulation therapy in the manner described above. For example, in response to the patient feedback, IMD 102 may suspend electrical stimulation according to the electrical stimulation therapy program having the high frequency for a predetermined amount of time. In another example, in response to the patient feedback, IMD 102 may commence electrical stimulation according to an electrical stimulation therapy program having a high frequency interleaved with an electrical stimulation therapy program having a low frequency for a predetermined amount of time. In another example, in response to the patient feedback, IMD 102 may suspend electrical stimulation according to the electrical stimulation therapy program having the high frequency, and commence electrical stimulation according to the electrical stimulation therapy program having a low frequency. As another example, in response to the patient feedback, IMD 102 interleaves the electrical stimulation therapy program having the high frequency with the electrical stimulation therapy program having the low frequency and deliver electrical stimulation according to the interleaved electrical stimulation therapy programs.

In additional examples, IMD 102 may control delivery of electrical stimulation therapy based on a signal received from one or more sensors 106. For example, IMD 102 may detect, via sensors 106, a level of one or more biomarkers of patient 112. Based on the level of the one or more biomarkers, IMD 102 may adjust one or more parameters of the electrical stimulation therapy in the manner described above. For example, a magnitude of a biomarker of patient 112 may correlate to a magnitude of one or more side effects of patient 112 evoked by the electrical stimulation therapy. In response to detecting a predetermined magnitude of the biomarker, IMD 102 may titrate one or more parameters defining the electrical stimulation therapy (e.g., frequency, pulse width, pulse amplitude) so as to reduce the magnitude of the biomarker, and thereby reduce the magnitude of the one or more side effects of patient 112.

In another example, a magnitude of a biomarker of patient 112 may correlate to an efficacy of the electrical stimulation therapy. Upon detecting a predetermined magnitude of the biomarker, IMD 102 may determine that the electrical stimulation therapy is providing more than a threshold level of control over the one or more symptoms of patient 112, and that one or more parameters defining the electrical stimulation therapy may be reduced to extend battery longevity of IMD 102 while still providing sufficient control over the one or more symptoms of patient 112. Accordingly, in response to detecting a predetermined magnitude of the biomarker, IMD 102 may titrate one or more parameters defining the electrical stimulation therapy (e.g., frequency, pulse width, pulse amplitude) so reduce the power consumption of IMD 102 while still providing sufficient control over the one or more symptoms of patient 112

The architecture of electrical stimulation system 100 illustrated in FIG. 1 is shown for exemplary purposes only. The techniques as set forth in this disclosure may be implemented in the example system 100 of FIG. 1, as well as other types of electrical stimulation systems not described specifically herein. For example, any of IMD 102, clinician programmer 104A, or patient programmer 104B may sense signals from the nerve fibers of the patient that are generated in response to the delivered electrical stimulation. In other examples, physiological signals generated from muscles (e.g., detected as an electrogram) may be used to determine the efficacy of delivered electrical stimulation. Further, any of IMD 102, clinician programmer 104A, or patient programmer 104B may determine a primary electrical stimulation parameter set and instruct IMD 102 to deliver future electrical stimulation according to the determined primary electrical stimulation parameter set. Additionally, the foregoing examples describe techniques for delivering electrical stimulation therapy. However, the techniques of the disclosure contemplate other types energies to drive neural stimulation. For example, instead of delivering electrical stimulation therapy, IMD 102 may alternatively be configured to deliver optical (e.g., laser, infrared, or ultraviolet light) stimulation therapy or ultrasonic stimulation therapy to treat the pelvic symptoms of patient 112.

Figure 2:
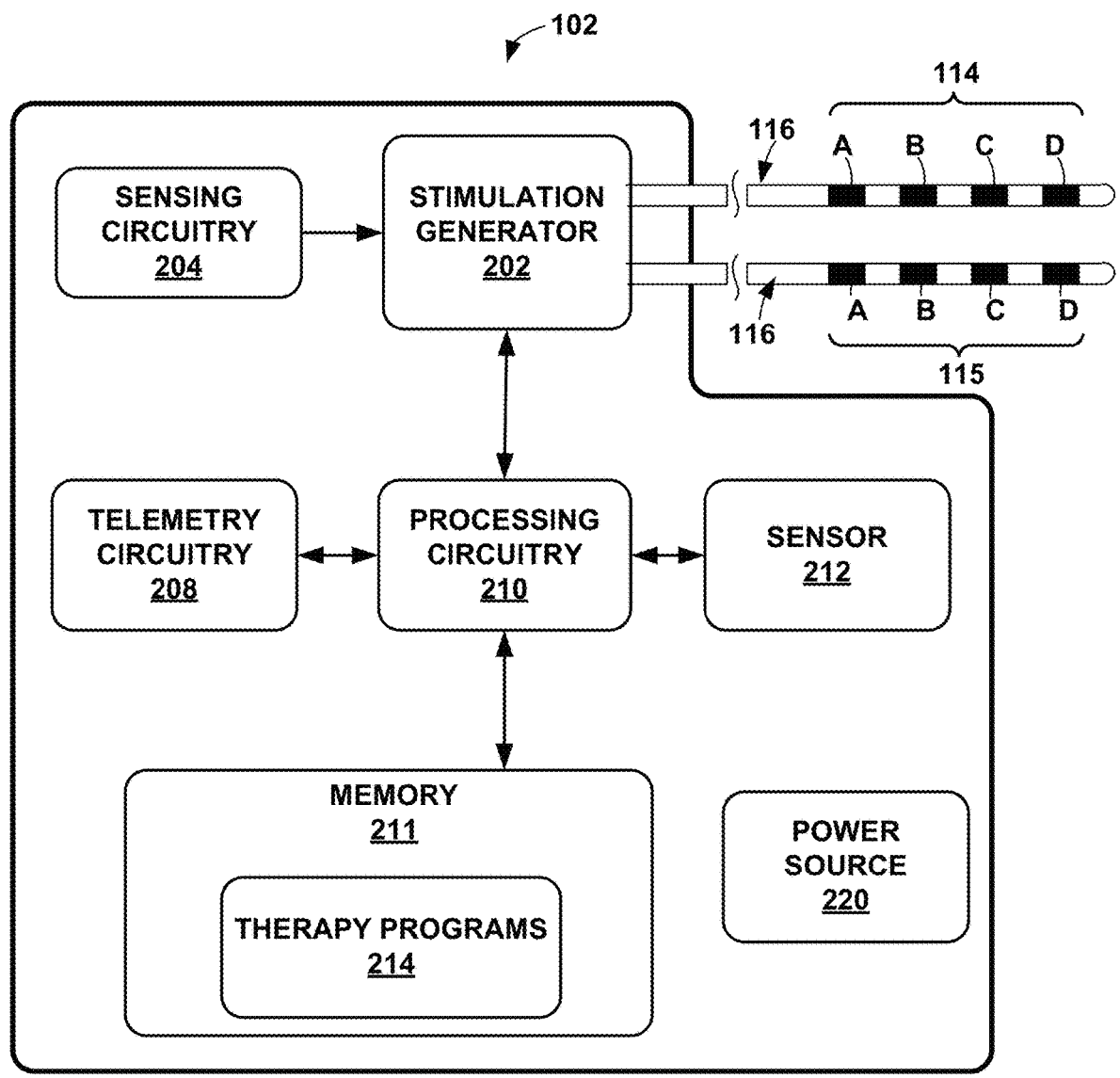
FIG. 2 is a block diagram of the example IMD of FIG. 1.

FIG. 2 is a block diagram of the example IMD 102 of FIG. 1. In the example shown in FIG. 2, IMD 102 includes processing circuitry 210, memory 211, stimulation generator 202, sensing circuitry 204, telemetry circuitry 208, sensor 212, and power source 220. Each of these circuitry blocks may be or include electrical circuitry configured to perform the functions attributed to each respective circuitry block. For example, processing circuitry 210 may include one or more processors, stimulation generator 202 may include switch circuitry, sensing circuitry 204 may include sensing circuitry, and telemetry circuitry 208 may include telemetry circuitry. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, the electrical stimulation parameters define a waveform for the electrical stimulation, such as rectangular or non-rectangular, rising exponentials, falling exponentials, or sinusoidal. Different waveforms may modulate the axon population differently, and may be selected so as to adjust the tissue area of patient 112 that receives electrical stimulation. In some examples, individual therapy programs may be stored as a therapy group, which defines a set of therapy programs with which stimulation may be generated. The stimulation signals defined by the therapy programs of the therapy group include stimulation pulses that may be delivered together on an overlapping or non-overlapping (e.g., time-interleaved) basis.

In some examples, processing circuitry 210 of IMD 102 controls stimulation generator 202 to deliver electrical stimulation therapy according to the one or more electrical stimulation therapy programs to patient 12 via a plurality of electrode combinations of electrodes 114, 115 of leads 16 at a high-frequency, such as a frequency selected from a range of greater than or equal to about 100 Hertz and less than or equal to about 50,000 Hertz. In other examples, processing circuitry 210 of IMD 102 delivers electrical stimulation therapy according to a plurality of lower-frequency electrical stimulation therapy programs to the patient 12 via a plurality of electrode combinations of electrodes 114, 115 of leads 16 and on a time-interleaved basis to effectively deliver combined, higher-frequency electrical stimulation to a target tissue site. Techniques for delivering such a combined, higher-frequency electrical stimulation to a target tissue site are described in more detail in U.S. patent application Ser. No. 15/623,141 to Nathan Torgerson, entitled "DELIVERY OF INDEPENDENT INTERLEAVED PROGRAMS TO PRODUCE HIGHER-FREQUENCY ELECTRICAL STIMULATION THERAPY" and filed on Jun. 14, 2017, the entire content of which is hereby incorporated by reference.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generator 202 according to therapy programs 214 stored in memory 211 to apply particular stimulation parameter values specified by one or more of programs, such as amplitude, pulse width, and pulse rate.

In the example shown in FIG. 2, the set of electrodes 114 includes electrodes 114A, 114B, 114C, and 114D, and the set of electrodes 115 includes electrodes 115A, 115B, 115C, and 115D. Processing circuitry 210 also controls stimulation generator 202 to generate and apply the stimulation signals to selected combinations of electrodes 114, 115. In some examples, stimulation generator 202 includes switch circuitry that couples stimulation signals to selected conductors within leads 16, which, in turn, deliver the stimulation signals across selected electrodes 114, 115. Such switch circuitry may be a switch array, switch matrix, multiplexer, or any other type of switching circuitry configured to selectively couple stimulation energy to selected electrodes 114, 115 and to selectively sense bioelectrical neural signals of spine 20 with selected electrodes 114, 115.

In other examples, however, stimulation generator 202 does not include switch circuitry. In these examples, stimulation generator 202 comprises a plurality of pairs of voltage sources, current sources, voltage sinks, or current sinks connected to each of electrodes 114, 115 such that each pair of electrodes has a unique signal generator. In other words, in these examples, each of electrodes 114, 115 is independently controlled via its own signal generator (e.g., via a combination of a regulated voltage source and sink or regulated current source and sink), as opposed to switching signals between electrodes 114, 115.

Stimulation generator 202 may be a single channel or multi-channel stimulation generator. In particular, stimulation generator 202 may be capable of delivering a single stimulation pulse or multiple stimulation pulses at a given time via a single electrode combination or multiple stimulation pulses at a given time via multiple electrode combinations. In some examples, however, stimulation generator 202 may be configured to deliver multiple channels on a time-interleaved basis. For example, switch circuitry of stimulation generator 202 may serve to time divide the output of stimulation generator 202 across different electrode combinations at different times to deliver multiple programs or channels of stimulation energy to patient 112. In another example, the stimulation generator 202 may control the independent sources or sinks on a time-interleaved bases. In some examples, stimulation generator 202 cycles through different stimulation parameters in blocks. In other examples, stimulation generator 202 interleaves different stimulation parameters with one another to create a composite electrical stimulation program. In yet further examples, stimulation generator 202 cycles between periods of time where electrical stimulation is delivered and periods of time wherein no electrical stimulation is delivered. In some examples, stimulation generator 202 includes circuitry configured to provide active or passive charge balancing so as to balancing electrical charge induced by delivery of the electrical stimulation.

Electrodes 114, 115 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. On one example, the electrodes may be electrically coupled to stimulation generator 202 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing circuitry 204 is incorporated into a common housing with stimulation generator 202 and processing circuitry 210 in FIG. 2, in other examples, sensing circuitry 204 may be in a separate housing from IMD 102 and may communicate with processing circuitry 210 via wired or wireless communication techniques. Example bioelectrical signals include, but are not limited to, a signal generated from local field potentials within one or more regions of spine 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to the patient).

Telemetry circuitry 208 supports wireless communication between IMD 102 and an external programmer 104 or another computing device under the control of processing circuitry 210. Processing circuitry 210 of IMD 102 may receive, as updates to programs, values for various stimulation parameters such as amplitude and electrode combination, from programmer 104 via telemetry circuitry 208. The updates to the therapy programs may be stored within therapy programs 214 portion of memory 211. Telemetry circuitry 208 in IMD 102, as well as telemetry circuitry in other devices and systems described herein, such as programmer 104, may accomplish communication by radiofrequency (RF) communication techniques. In addition, telemetry circuitry 208 may communicate with external medical device programmer 104 via proximal inductive interaction of IMD 102 with programmer 104. Accordingly, telemetry circuitry 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow 220 to utilize patient motion and implement a kinetic energy-scavenging device to trickle charge a rechargeable battery. In other examples, traditional batteries may be used for a limited period of time.

According to the techniques of the disclosure, telemetry circuitry 208 of IMD 102 receives commands from an external programmer 104. In response to these commands, processing circuitry 210 of IMD 102 controls stimulation generator 202 to deliver electrical stimulation therapy programs to a target tissue area of the spinal column 20 of patient 112 via electrodes 114, 115 of leads 16.

As discussed earlier, the techniques of the disclosure make use of the unexpected and surprising discovery that high frequency electrical stimulation therapy does not induce substantial side effects in patients and has shown to provide improvements in certain therapeutic effects, relative to conventional low frequency electrical stimulation. This can include, for example, improvements to the ability to inhibit bladder contractions. For example, the high frequency electrical stimulation therapy may have a frequency of greater than about 100 Hertz in some examples, greater than about 500 Hertz in further examples, greater than about 800 Hertz in still further examples, and greater than or equal to about 1,000 Hertz in still further examples. Additionally, the high frequency electrical stimulation therapy may have a frequency of less than about 50,000 Hertz in some examples, less than about 30,000 Hertz in further examples, less than about 20,000 Hertz in further examples, less than about 5,000 Hertz in further examples, and less than about 3,000 Hertz in still further examples. In some examples, the high frequency electrical stimulation therapy may have a frequency greater than about 100 Hertz and less than about 50,000 Hertz, greater than about 500 Hertz and less than about 20,000 Hertz in other examples, greater than about 500 Hertz and less than about 5,000 Hertz in other examples, greater than about 800 Hertz and less than about 3,000 Hertz in still further examples, or greater than or equal to about 1,000 Hertz and less than or equal to about 3,000 Hertz in still further examples. In some examples, the high frequency electrical stimulation therapy may have a frequency greater than or equal to about 1,000 Hertz and less than or equal to about 5,000 Hertz. In some examples, the high frequency electrical stimulation therapy may have a frequency of about 1,000 Hertz.

Experimental results suggest improved bladder capacity can be achieved using electrical stimulation therapy having a frequency greater than 100 Hertz and less than 5,000 Hertz. Moreover, the experimental results suggest that frequencies of around 1000 Hertz may exhibit bladder capacities with improvements several times more than the improvements seen at traditional (e.g., 10 Hertz) stimulation frequencies. It is expected that further testing may result in further refinement of the optimal stimulation frequencies. For example, further testing may find further improvement in bladder capacity at frequencies below 1,000 Hertz and above 100 Hertz. Various embodiments therefore contemplate the use of frequencies in this range, such as from about 500 Hertz to about 900 Hertz. Moreover, further testing may find further improvement in bladder capacity at frequencies above 1,000 Hertz and below 5,000 Hertz. Various embodiments therefore contemplate the use of frequencies in this range, such as from about 1,100 Hertz to about 4,000 Hertz.

Certain embodiments recognize that the optimal frequency may vary from patient to patient, e.g., due to differences in implant location, patient morphology, or other factors. Accordingly, certain embodiments are directed toward a medical device that can adjust the stimulation frequency delivered to the patient allowing for feedback on the effectiveness to be used in selection of the stimulation frequency. For instance, a patient or clinician can provide feedback on the effectiveness of a treatment operating at a first stimulation frequency. The medical device can then be used to adjust the stimulation frequencies up or down. The patient or clinician can provide feedback on the effectiveness at the new frequency. This process can continue, for example, until the adjustment fails to provide further improvement, or until a predetermined set of frequencies has been tested. The medical device can then be configured to provide stimulation at a frequency that is responsive to the findings of this process. In certain implementations, the medical device can be configured to adjust the stimulation frequency between one or more of the ranges described herein. Various embodiments include a medical device configured to include stimulation at lower frequencies (e.g., below 100 Hertz) as part of stimulation and the feedback process described above.

In some examples, the high frequency electrical stimulation therapy is interleaved or combined with a low frequency electrical stimulation therapy. The low frequency electrical stimulation therapy may have a frequency of greater than about 1 Hertz in some examples, and greater than 10 Hertz in other examples. Additionally, the low frequency electrical stimulation therapy may have a frequency of less than about 50 Hertz in some examples, and less than 20 Hertz in other examples. In some examples, the low frequency electrical stimulation therapy may have a frequency greater than or equal to about 1 Hertz and less than or equal to about 50 Hertz, greater than or equal to about 10 Hertz and less than or equal to about 20 Hertz in other examples, or greater than or equal to about 10 Hertz and less than or equal to about 15 Hertz in still other examples.

According to the techniques of this disclosure, processing circuitry 210 controls stimulation generator 202 to deliver electrical stimulation therapy to a target tissue site of patient 112 to provide therapy for one or more pelvic symptoms of patient 112. Processing circuitry 210 controls stimulation generator 202 to deliver the electrical stimulation according to at least one therapy program. In one example, processing circuitry 210 controls stimulation generator 202 to deliver electrical stimulation according to a first electrical stimulation therapy program having a high frequency (e.g., a frequency greater than or equal to about 100 Hertz) to provide therapy for one or more pelvic symptoms of patient 112. In some examples, processing circuitry 210 controls stimulation generator 202 to deliver a combined electrical stimulation therapy according to a duty cycle having periods of delivery of electrical stimulation pulses interleaved with periods of non-delivery of electrical stimulation pulses. In some examples, processing circuitry 210 controls stimulation generator 202 to deliver continuous electrical stimulation therapy according a primary frequency component. Thus, such a system for delivering electrical stimulation having a high frequency may provide better therapy for the one or more pelvic symptoms of patient 112 than other systems that deliver electrical stimulation having a low frequency (e.g., a frequency less than about 50 Hertz). For example, such a system as described herein may provide better bladder control or enhanced assistance with bladder voiding than other systems.

As an example of a system for providing bladder control, processing circuitry 210 controls stimulation generator 202 to deliver, during normal operation, electrical stimulation according to a first electrical stimulation therapy program having a high frequency (e.g. a frequency greater than or equal to about 100 Hertz). In one example, the high frequency is selected from a range of frequencies from about 1,000 Hertz to about 5,000 Hertz. Upon sensing a urinary activity of patient 112, processing circuitry 210 controls stimulation generator 202 to suspend delivery of electrical stimulation according to the first electrical stimulation therapy program having the high frequency (e.g., a frequency greater than or equal to about 100 Hertz). Thus, such a system delivers, during normal operation, electrical stimulation having the high frequency to assist in bladder control (e.g., to suppress pelvic and bladder muscle contractions) of patient 112. Upon detecting that patient 112 is undergoing, or attempting to undergo, a voiding event, processing circuitry 210 controls stimulation generator 202 to suspend delivery of electrical stimulation, which reduces control of bladder contractions and assists patient 112 in completing the voiding event. Processing circuitry 210 may detect the urinary activity by receiving input from external programmer 104, feedback from patient 112 regarding the commencement or completion of urinary activity, or a signal from one or more sensors 106 and 212 indicating a change in state, posture, or activity of patient 112. Upon determining that the urinary activity has completed, processing circuitry 210 controls stimulation generator 202 to resume the electrical stimulation having the high frequency so as to resume suppression of pelvic and bladder muscle contractions of patient 112.

In alternate examples, during normal operation, electrical stimulation is delivered according to the first electrical stimulation therapy program having the high frequency and interleaved with a second electrical stimulation therapy program having a low frequency (e.g. a frequency less than about 50 Hertz). Upon sensing a urinary activity of patient 112, processing circuitry 210 controls stimulation generator 202 to suspend delivery of the electrical stimulation, which reduces control of bladder contractions and assists patient 112 in completing the voiding event. Processing circuitry 210 may detect the urinary activity by receiving input from external programmer 104, feedback from patient 112 regarding the commencement or completion of urinary activity, or a signal from one or more sensors 106 and 212 indicating a change in state, posture, or activity of patient 112. Upon determining that the urinary activity has completed, processing circuitry 210 controls stimulation generator 202 to resume the electrical stimulation having the high frequency interleaved with the second electrical stimulation therapy program having the low frequency so as to resume suppression of pelvic and bladder muscle contractions of patient 112.

In some examples, in response to detecting that the urinary activity has ceased, processing circuitry 210 controls stimulation generator 202 to resume normal electrical stimulation therapy (e.g., electrical stimulation therapy according to the electrical stimulation therapy program having a high frequency). In such examples, processing circuitry 210 may control stimulation generator 202 to resume electrical stimulation therapy having the high frequency immediately, or gradually increase one of a current amplitude or a voltage amplitude of the electrical stimulation therapy having the high frequency. In other examples, processing circuitry 210 controls stimulation generator 202 to resume or gradually increase the electrical stimulation therapy according to the electrical stimulation therapy program having the high frequency after a predetermined amount of time. Such a predetermined amount of time may allow the patient to complete a bladder or fecal voiding event before processing circuitry 210 controls stimulation generator 202 to resumes the normal electrical stimulation therapy.

As an example of a system for providing both bladder control and assistance with bladder voiding, processing circuitry 210 controls stimulation generator 202 to deliver, during normal operation, electrical stimulation according to the first electrical stimulation therapy program having the high frequency (e.g., a frequency greater than or equal to about 100 Hertz). In one example, the high frequency is selected from a range of frequencies from about 1,000 Hertz to about 5,000 Hertz. Upon sensing a urinary activity of patient 112, processing circuitry 210 controls stimulation generator 202 to deliver electrical stimulation according to a second electrical stimulation therapy program having a low frequency (e.g. a frequency less than about 50 Hertz) and suspend delivery of electrical stimulation according to the first electrical stimulation therapy program having the high frequency. Thus, such a system delivers, during normal operation, electrical stimulation having the high frequency to assist in bladder control (e.g., to suppress pelvic and bladder muscle contractions) of patient 112. Upon detecting that patient 112 is undergoing, or attempting to undergo, a voiding event, processing circuitry 210 controls stimulation generator 202 to deliver electrical stimulation having the low frequency, which may evoke bladder contractions and assist patient 112 in completing the voiding event. Processing circuitry 210 may detect the urinary activity by receiving input from external programmer 104, feedback from patient 112 regarding the commencement or completion of urinary activity, or a signal from one or more sensors 106 and 212 indicating a change in state, posture, or activity of patient 112. Upon determining that the urinary activity has completed, processing circuitry 210 controls stimulation generator 202 to discontinue the electrical stimulation having the low frequency and resume electrical stimulation having the high frequency so as to resume suppression of pelvic and bladder muscle contractions of patient 112.

While in the above example, processing circuitry 210 controls stimulation generator 202 to alternate between delivery of electrical stimulation having the high frequency or electrical stimulation having the low frequency, the techniques of the disclosure also contemplate delivering electrical stimulation according to an electrical stimulation program having a high frequency interleaved with an electrical stimulation program having a low frequency. As one example, processing circuitry 210 controls stimulation generator 202 to interleave the first electrical stimulation therapy program having the high frequency (e.g., a frequency greater than or equal to about 100 Hertz) with the second electrical stimulation therapy program having the low frequency (e.g., a frequency less than or equal to about 50 Hertz), and controls delivery of the electrical stimulation to patient 112 according to the interleaved first and second electrical stimulation therapy programs. Such a combined electrical stimulation therapy may suppress one or more symptoms of the pelvic symptoms of patient 112 in a manner more effective than electrical stimulation having a low frequency alone, while reducing or preventing side effects of the electrical stimulation therapy, such as paresthesia.

In yet another example of interleaved electrical stimulation, during normal operation, processing circuitry 210 controls stimulation generator 202 to continuously deliver electrical stimulation therapy according to an electrical stimulation therapy program having the high frequency (e.g., a frequency greater than or equal to about 100 Hertz). Upon detecting that patient 112 is undergoing, or attempting to undergo, a urinary activity, processing circuitry 210 adjusts one or more parameters defining the electrical stimulation therapy. Processing circuitry 210 may detect the urinary activity by receiving input from external programmer 104, feedback from patient 112 regarding the commencement or completion of urinary activity, or a signal from one or more sensors 106 and 212 indicating a change in state, posture, or activity of patient 112. For example, in response to a signal from sensors 106 and 212 indicating a commencement of urinary activity of patient 112, processing circuitry 210 controls stimulation generator 202 to interleave the electrical stimulation therapy program having the high frequency with an electrical stimulation therapy program having a low frequency (e.g., a frequency less or equal to than about 50 Hertz), and deliver electrical stimulation therapy according to the interleaved electrical stimulation therapy programs. Alternatively, in response to feedback from patient 112 indicating that a urinary activity of patient 112 has commenced or is about to commence, processing circuitry 210 controls stimulation generator 202 to interleave the electrical stimulation therapy program having the high frequency and the electrical stimulation therapy program having the low frequency, and deliver electrical stimulation therapy according to the interleaved electrical stimulation therapy programs. Furthermore, while in some examples, processing circuitry 210 controls stimulation generator 202 to interleave the electrical stimulation therapy program having the high frequency with the electrical stimulation therapy program having the high frequency, each electrical stimulation program being interleaved at a maximum amplitude, in other examples, processing circuitry 210 controls stimulation generator 202 to interleave the electrical stimulation therapy programs by gradually increasing an amplitude (e.g., one of a voltage amplitude or a current amplitude) of at least one of the electrical stimulation therapy program having the low frequency and the electrical stimulation therapy program having the high frequency. In some examples of the above techniques, processing circuitry 210 adjusts the one or more parameters defining the electrical stimulation therapy slightly before the urinary activity commences. In still further examples, processing circuitry 210 adjusts the one or more parameters defining the electrical stimulation therapy slightly after the urinary activity commences.

In a still further example, processing circuitry 210 controls stimulation generator 202 to periodically adjust the electrical stimulation therapy delivered to patient 112. As one example, processing circuitry 210 controls stimulation generator 202 to periodically switch from delivery of electrical stimulation therapy according to an electrical stimulation therapy program having a low frequency (e.g., a frequency less than or equal to about 50 Hertz) to delivery of electrical stimulation therapy according to an electrical stimulation therapy program having a high frequency (e.g., a frequency greater than or equal to about 100 Hertz). In another example, processing circuitry 210 controls stimulation generator 202 to continuously deliver electrical stimulation therapy according to the electrical stimulation therapy program having the low frequency (e.g., a frequency less than or equal to about 50 Hertz). In this example, processing circuitry 210 controls stimulation generator 202 to periodically interleave the electrical stimulation therapy program having the high frequency (e.g., a frequency greater than or equal to about 100 Hertz) with the electrical stimulation therapy program having the low frequency and deliver the interleaved electrical stimulation to patient 112. However, in other examples, processing circuitry 210 may control stimulation generator 202 to deliver electrical stimulation according to only one of the electrical stimulation therapy program having the low frequency and the electrical stimulation therapy program having the high frequency. In some examples, processing circuitry 210 makes such periodical adjustments after a predetermined time has elapsed, according to a predetermined schedule, or upon sensing, via electrodes 114, 115, that a state of patient 112 has changed (e.g., such as changes in the impedance of electrodes 114, 115 or tissue of patient 112).

In some examples, in response to detecting that the urinary activity has ceased, processing circuitry 210 controls stimulation generator 202 to discontinue electrical stimulation therapy according to the electrical stimulation therapy program having the low frequency and resume normal electrical stimulation therapy (e.g., electrical stimulation therapy according to the electrical stimulation therapy program having the high frequency). In such examples, processing circuitry 210 may control stimulation generator 202 to immediately discontinue electrical stimulation therapy having the low frequency immediately, or gradually decrease one of a current amplitude or a voltage amplitude of the electrical stimulation therapy having the low frequency. In other examples, processing circuitry 210 controls stimulation generator 202 to discontinue or gradually reduce the electrical stimulation therapy according to the electrical stimulation therapy program having the low frequency after a predetermined amount of time. Such a predetermined amount of time may allow the patient to complete a bladder or fecal voiding event before processing circuitry 210 controls stimulation generator 202 to resumes the normal electrical stimulation therapy.

The architecture of IMD 102 illustrated in FIG. 2 is shown as an example. The techniques as set forth in this disclosure may be implemented in the example IMD 102 of FIG. 2, as well as other types of systems not described specifically herein. Nothing in this disclosure should be construed so as to limit the techniques of this disclosure to the example architecture illustrated by FIG. 2.

Figure 3:
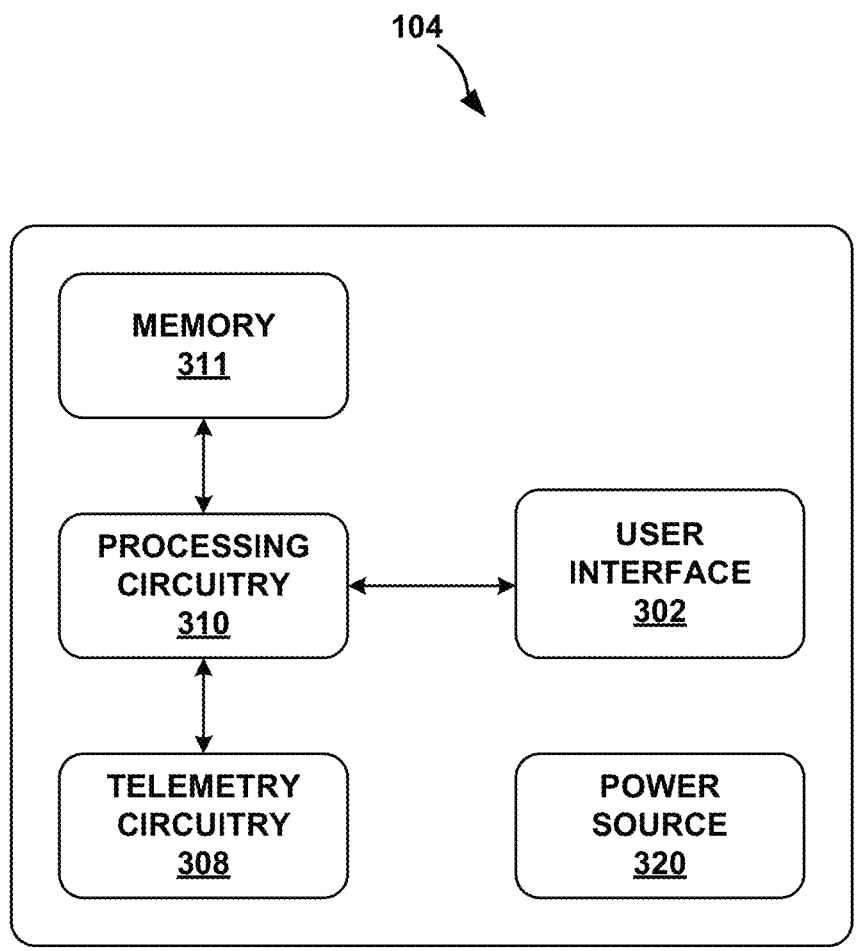
FIG. 3 is a block diagram of the example external programmer of FIG. 1.

FIG. 3 is a block diagram of an example external programmer 104 of FIG. 1, such as programmer 104A or programmer 104B. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or circuitry, may include electrical circuitry that is configured to perform some or all of the functionality described herein. For example, processing circuitry 310 may include one or more processors configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate circuits, in some examples, processing circuitry 310 and telemetry circuitry 308 are functionally integrated. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain a parameter set from memory, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, or the input may request some other change to the delivery of electrical stimulation.

Telemetry circuitry 308 may support wireless communication between IMD 102 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry circuitry 308 may be configured to transmit stimulation parameter values to IMD 102 for delivery of stimulation therapy.

In some examples, programmer 104 may use telemetry circuitry 308 to provide a selection of therapy parameters or therapy programs to IMD 102. In other examples, the selection of therapy parameters or therapy programs may include medication, activities, or other instructions that patient 112 must perform themselves or a caregiver perform for patient 112. In some examples, programmer 104 may provide visual, audible, and/or tactile notifications, e.g., via user interface 302, that indicate there are new instructions. Programmer 104 may require receiving user input, e.g., via user interface 302, acknowledging that the instructions have been completed in some examples.

According to the techniques of the disclosure, processing circuitry 310, in response to commands received from a clinician or patient via user interface 302, may transmit commands via telemetry circuitry 308 causing IMD 102 to deliver electrical stimulation therapy to a target tissue site of patient 112 to provide therapy for one or more pelvic symptoms of patient 112. Processing circuitry 310 causes IMD 102 to deliver the electrical stimulation according to at least one therapy program. As discussed earlier, the techniques of the disclosure make use of the unexpected and surprising discovery that electrical stimulation delivered according to an electrical stimulation therapy program comprising a high frequency does not induce substantial side effects in patients and has shown improved therapeutic efficacy relative to electrical stimulation delivered according to a conventional electrical stimulation therapy program comprising a low frequency. For example, processing circuitry 310 causes IMD 102 to deliver a first electrical stimulation therapy program having a high frequency (e.g., a frequency greater than or equal to about 100 Hertz) to patient 112. In some examples, the high frequency is a frequency selected from a range greater than or equal to about 1,000 Hertz and less than or equal to about 5,000 Hertz. In further examples, the high frequency is 1,000 Hertz. Such a high frequency electrical stimulation therapy may suppress one or more of the pelvic symptoms of patient 112 in a fashion more effective than electrical stimulation therapy having a low frequency (e.g., less than or equal to 50 Hertz) or frequencies greater than or equal to 5,000 Hertz.

In further examples, processing circuitry 310 causes IMD 102 to interleave a first electrical stimulation therapy program having a high frequency (e.g., a frequency greater than or equal to about 100 Hertz) and a second electrical stimulation therapy program having a low frequency (e.g. a frequency less than or equal to about 50 Hertz), and deliver the electrical stimulation to patient 112 according to the interleaved first and second electrical stimulation therapy programs. Such a combined electrical stimulation therapy may suppress one or more symptoms of the pelvic symptoms of patient 112 in a fashion more effective than electrical stimulation therapy having a low frequency alone.

In one example of a system for providing bladder control, IMD 102 continuously delivers electrical stimulation therapy according to an electrical stimulation therapy program having the high frequency. Alternatively, IMD 102 may interleave the electrical stimulation therapy program having the low frequency with the electrical stimulation therapy program having the high frequency, and delivers electrical stimulation therapy according to the interleaved electrical stimulation therapy programs. IMD 102 may deliver the electrical stimulation therapy according to a duty cycle having periods of delivery of electrical stimulation pulses interleaved with periods of non-delivery of electrical stimulation pulses. In one example, processor receives feedback from patient 112 indicating a urinary activity. In response to such feedback, processing circuitry 310 transmits, via telemetry circuitry 308, commands to IMD 102 causing IMD 102 to adjust delivery of the electrical stimulation therapy. For example, as described above, IMD 102 may suspend delivery of the electrical stimulation according to the electrical stimulation therapy program having the high frequency for a predetermined amount of time. In other examples, IMD 102 may adjust one or more parameters defining the electrical stimulation.

In some examples, in response to receiving feedback from patient 112 that the urinary activity has ceased, processing circuitry 310 transmits, via telemetry circuitry 308, commands to IMD 102 causing IMD 102 to resume normal electrical stimulation therapy (e.g., electrical stimulation therapy according to the electrical stimulation therapy program having a high frequency). In other examples, IMD 102 automatically resumes electrical stimulation therapy according to the electrical stimulation therapy program having a high frequency after a predetermined amount of time. Such a predetermined amount of time may allow the patient to complete a bladder or fecal voiding event before IMD 102 resumes the normal electrical stimulation therapy, without relying on commands from external programmer 104.

In an example of a system for providing both bladder control and voiding assistance, IMD 102 continuously delivers electrical stimulation therapy according to an electrical stimulation therapy program having the low frequency. IMD 102 may deliver the electrical stimulation therapy according to a duty cycle having periods of delivery of electrical stimulation pulses interleaved with periods of non-delivery of electrical stimulation pulses. In one example, processor receives feedback from patient 112 indicating a urinary activity. In response to such feedback, processing circuitry 310 transmits, via telemetry circuitry 308, commands to IMD 102 causing IMD 102 to adjust delivery of the electrical stimulation therapy. For example, as described above, IMD 102 may suspend according to the electrical stimulation therapy program having the low frequency, and begin delivery of electrical stimulation therapy according to an electrical stimulation therapy program having a high frequency. Alternatively, IMD 102 may interleave the electrical stimulation therapy program having the low frequency with the electrical stimulation therapy program having the high frequency, and delivers electrical stimulation therapy according to the interleaved electrical stimulation therapy programs. In yet further examples, IMD 102 may gradually increase an amplitude of the electrical stimulation therapy program having the high frequency when interleaving the electrical stimulation therapy program having a high frequency with the electrical stimulation therapy program having the low frequency so as to gradually increase the amplitude of the electrical stimulation therapy program having a high frequency delivered to patient 112.

In some examples, in response to receiving feedback from patient 112 that the urinary activity has ceased, processing circuitry 310 transmits, via telemetry circuitry 308, commands to IMD 102 causing IMD 102 to discontinue electrical stimulation therapy according to the electrical stimulation therapy program having a high frequency and resume normal electrical stimulation therapy (e.g., electrical stimulation therapy according to the electrical stimulation therapy program having a low frequency). In other examples, IMD 102 automatically discontinues electrical stimulation therapy according to the electrical stimulation therapy program having a high frequency after a predetermined amount of time. Such a predetermined amount of time may allow the patient to complete a bladder or fecal voiding event before IMD 102 resumes the normal electrical stimulation therapy, without relying on commands from external programmer 104.

The architecture of programmer 104 illustrated in FIG. 3 is shown as an example. The techniques as set forth in this disclosure may be implemented in the example programmer 104 of FIG. 3, as well as other types of systems not described specifically herein. Nothing in this disclosure should be construed so as to limit the techniques of this disclosure to the example architecture illustrated by FIG. 3.

Figure 4:
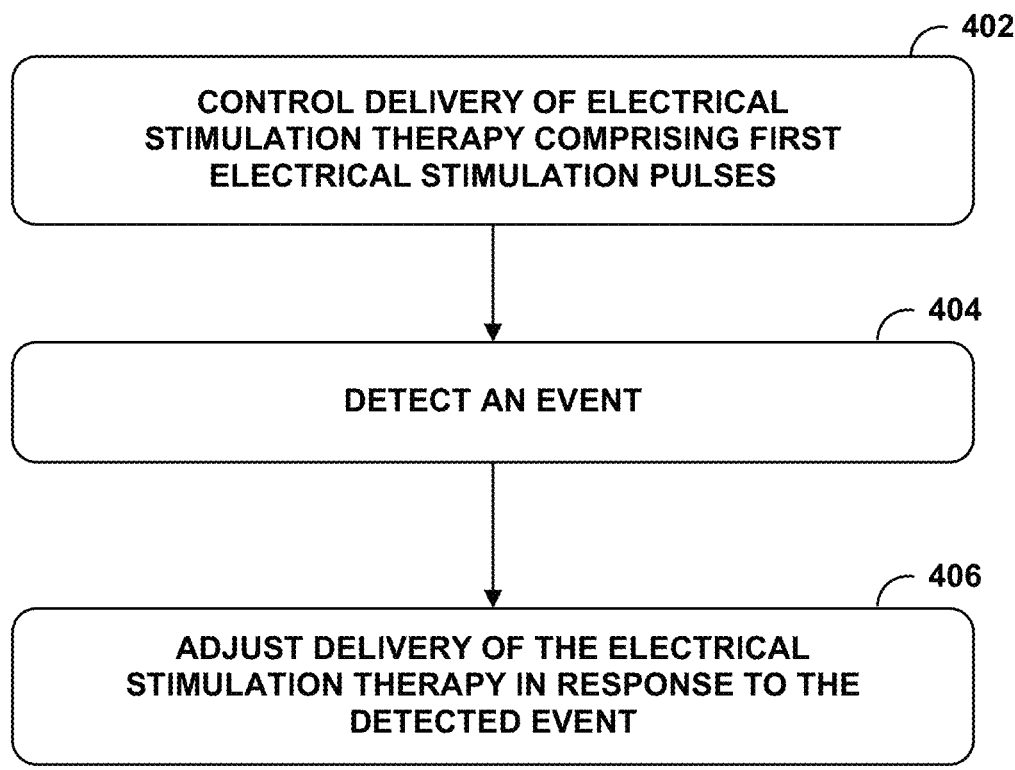
FIG. 4 is a flowchart depicting an example operation for the IMD of FIG. 1.

FIG. 4 is an illustration depicting an example operation for the IMD 102 of FIG. 1. For ease of description, FIG. 4 is described with respect to FIGS. 1 and 2. As discussed earlier, the techniques of the disclosure make use of the unexpected and surprising discovery that electrical stimulation delivered according to an electrical stimulation therapy program comprising a high frequency does not induce substantial side effects in patients and has shown improved therapeutic efficacy in patients relative to electrical stimulation delivered according to a conventional electrical stimulation therapy program comprising a low frequency.

As depicted in FIG. 4, processing circuitry 210 of IMD 102 controls stimulation generator 202 to deliver an electrical stimulation therapy comprising first electrical stimulation pulses at a first frequency greater than or equal to about 100 Hertz and less than or equal to about 50,000 Hertz (402). In one example, the first electrical stimulation pulses have a pulse width of 100 microseconds and an amplitude sufficient to evoke muscle contraction in patient 112.

Next, processing circuitry 210 detects that an event has occurred (404). Examples of such an event include a urinary activity, a change in activity of patient 112, a movement of patient 112, a posture change of patient 112, a time of day, signals from sensors 106 or 212, feedback from patient 112, commands from external programmer 104, or the change of a therapeutic delivery schedule, and the like. As one example, processing circuitry 210 receives a signal from sensors 106 or 212 indicating that patient 112 is undergoing a bladder voiding event, a bladder filling event, or a bladder contraction. In other examples, processing circuitry 210 may receive, from sensors 106 or 212, a signal indicating spatial, locational, or temporal information about patient 112. In another example, processing circuitry 210 receives feedback from patient 112 indicating that a urinary activity of patient 112 has commenced or completed. In a still further example, a therapeutic delivery schedule changes from delivery of a first type of electrical stimulation to delivery of a second type of electrical stimulation.

In response to the detected event, processing circuitry 210 of IMD 102 controls stimulation generator 202 to adjust one or more parameters of the electrical stimulation therapy (406). For example, upon detecting that patient 112 is undergoing a urinary activity, processing circuitry 210 of IMD 102 controls stimulation generator 202 to adjust one of a current amplitude or a voltage amplitude of the first electrical stimulation pulses. In other examples, processing circuitry 210 controls stimulation generator 202 to adjust the frequency of the first electrical stimulation pulses (e.g., to suspend delivery of the electrical stimulation pulses at 1,000 Hertz, or to commence delivery of the electrical stimulation pulses at 1,000 Hertz instead of 100 Hertz). In further examples, processing circuitry 210 controls stimulation generator 202 to adjust a pulse width of the first electrical stimulation pulses. In yet further examples, processing circuitry 210 controls stimulation generator 202 to interleave delivery of the first electrical pulses with second electrical pulses at a second frequency greater than about 1 Hertz and less than about 50 Hertz. In yet further examples, processing circuitry 210 controls stimulation generator 202 to interleave delivery of the first electrical pulses with periods of no electrical stimulation. In further examples, processing circuitry 210 controls stimulation generator 202 to suspend delivery of the first electrical pulses and commence delivery of the second electrical pulses at a second frequency greater than about 1 Hertz and less than about 50 Hertz. In further examples, processing circuitry 210 controls stimulation generator 202 to suspend delivery of the first electrical pulses and deliver no electrical stimulation therapy for a predetermined amount of time.

Figure 5:
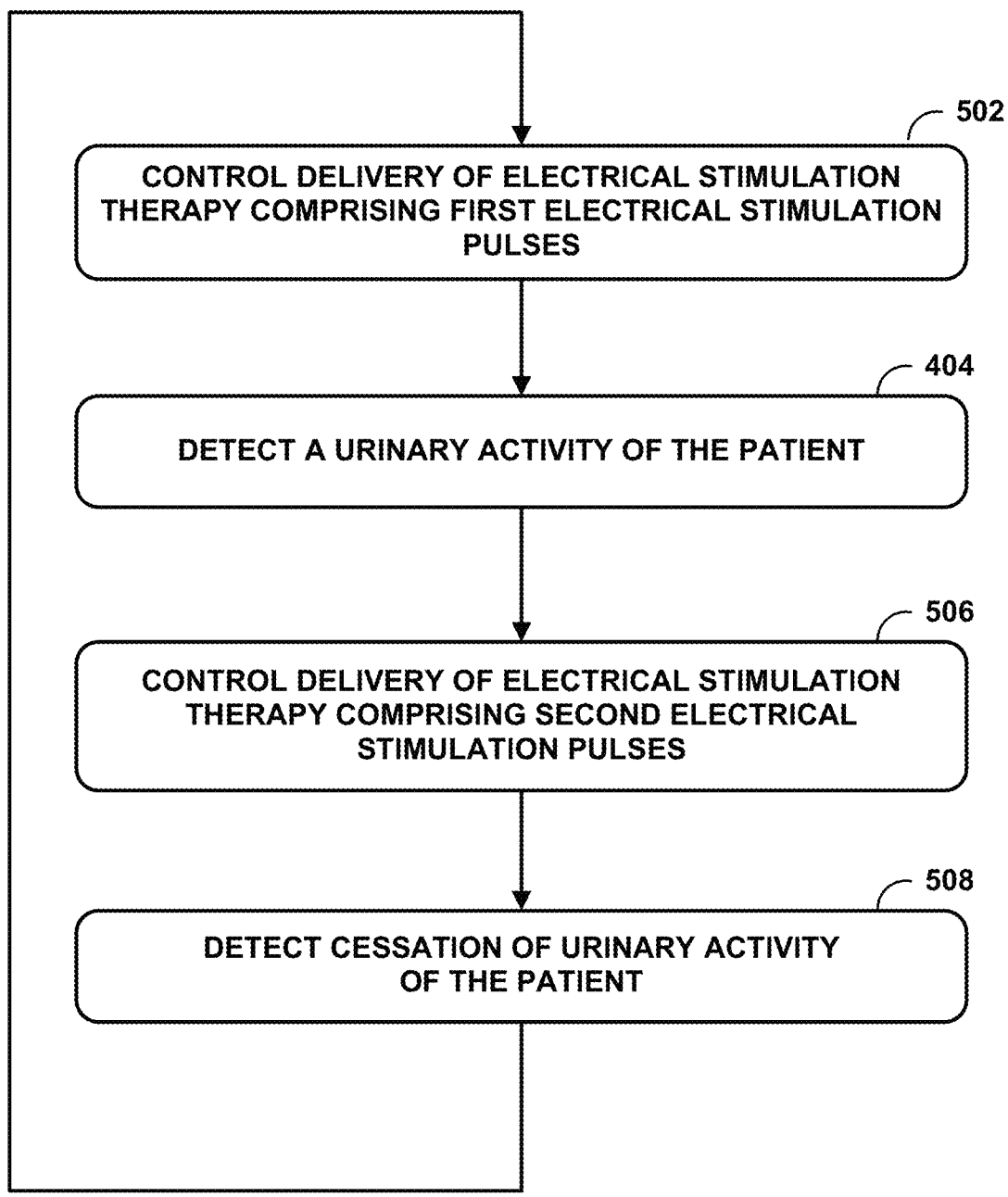
FIG. 5 is a flowchart depicting an example operation for the IMD of FIG. 1.

FIG. 5 is an illustration depicting an example operation for the IMD 102 of FIG. 1. For ease of description, FIG. 5 is described with respect to FIGS. 1 and 2. As discussed earlier, the techniques of the disclosure make use of the unexpected and surprising discovery that electrical stimulation delivered according to an electrical stimulation therapy program comprising the high frequency does not induce substantial side effects in patients and has shown improved therapeutic efficacy in patients relative to electrical stimulation delivered according to a conventional electrical stimulation therapy program comprising a low frequency.

As depicted in FIG. 5, processing circuitry 210 of IMD 102 controls stimulation generator 202 to deliver an electrical stimulation therapy comprising first electrical stimulation pulses at a first frequency greater than or equal to about 100 Hertz and less than about 50,000 Hertz (502). In some examples, the first frequency is greater than or equal to about 1,000 Hertz and less than or equal to about 5,000 Hertz. In other examples, the first frequency is 1,000 Hertz. Processing circuitry 210 receives, via telemetry circuitry 208, a signal indicative of a urinary activity of patient 112 (404), as described above with respect to FIG. 4. In alternative examples, instead of detecting a urinary activity of the patient, processing circuitry 210 may receive, from sensors 106, a signal indicating spatial, locational, or temporal information about patient 112. In still further examples, instead of detecting a urinary activity of the patient, processing circuitry 210 may receive feedback from patient 112 indicating the commencement of urinary activity.

In response to the detected urinary activity, processing circuitry 210 of IMD 102 controls stimulation generator 202 to cease delivery of the electrical stimulation therapy comprising the first electrical stimulation pulses and deliver electrical stimulation therapy comprising second electrical stimulation pulses at a second frequency greater than about 1 Hertz and less than about 50 Hertz (506). In some examples, processing circuitry 210 of IMD 102 gradually increases one of a voltage amplitude or a current amplitude of the second electrical stimulation pulses so as to prevent discomfort or side effects in patient 112 due to rapid changes in the electrical stimulation therapy. Further, in some examples, processing circuitry 210 of IMD 102 gradually decreases one of a voltage amplitude or a current amplitude of the first electrical stimulation pulses so as to prevent discomfort or side effects in patient 112 due to rapid changes in the electrical stimulation therapy.

In response to detecting that the urinary activity has ceased (508), processing circuitry 210 of IMD 102 controls stimulation generator 202 to cease delivery of the electrical stimulation therapy comprising the second electrical stimulation pulses and deliver electrical stimulation therapy comprising the first electrical stimulation pulses (502). In alternative examples, processing circuitry 210 of IMD 102 continues delivery of the electrical stimulation therapy comprising the second electrical stimulation pulses for a predetermined time. Upon expiration of the predetermined time, processing circuitry 210 of IMD 102 controls stimulation generator 202 to cease delivery of the electrical stimulation therapy comprising the second electrical stimulation pulses and deliver electrical stimulation therapy comprising the first electrical stimulation pulses (502). As described above, in some example, processing circuitry 210 of IMD 102 gradually decreases one of a voltage amplitude or a current amplitude of the second electrical stimulation pulses and/or gradually increases one of a voltage amplitude or a current amplitude of the first electrical stimulation pulses so as to prevent discomfort or side effects in patient 112 due to rapid changes in the electrical stimulation therapy.

Figure 6:
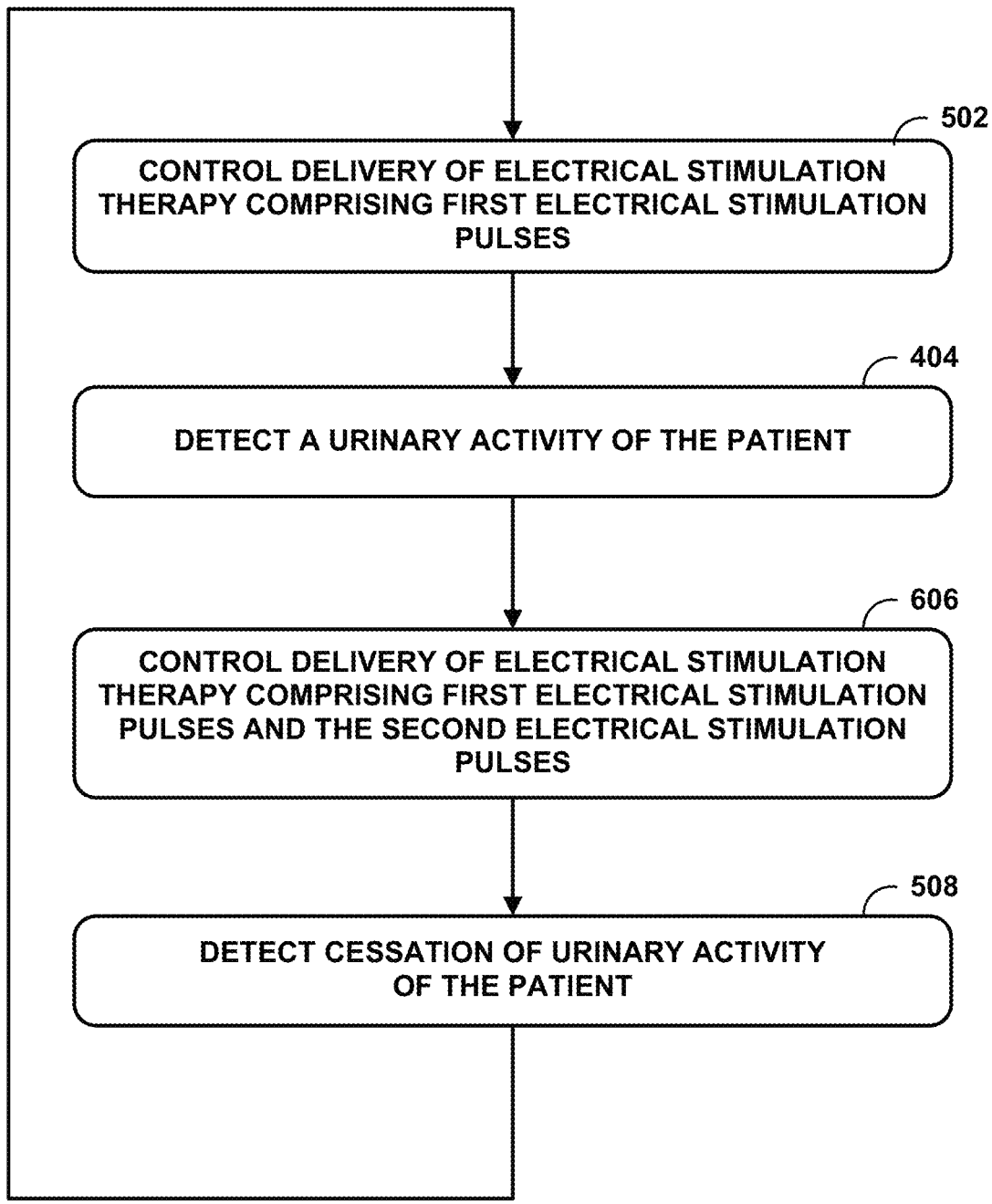
FIG. 6 is a flowchart depicting an example operation for the IMD of FIG. 1.

FIG. 6 is an illustration depicting an example operation for the IMD 102 of FIG. 1. For ease of description, FIG. 6 is described with respect to FIGS. 1 and 2. As discussed earlier, the techniques of the disclosure make use of the unexpected and surprising discovery that electrical stimulation delivered according to an electrical stimulation therapy program comprising the high frequency does not induce substantial side effects in patients and has shown improved therapeutic efficacy in patients relative to electrical stimulation delivered according to a conventional electrical stimulation therapy program comprising a low frequency.

As depicted in the example of FIG. 6, processing circuitry 210 of IMD 102 controls stimulation generator 202 to deliver an electrical stimulation therapy comprising first electrical stimulation pulses at a first frequency greater than about 100 Hertz and less than about 20,000 Hertz (502), as described above with respect to FIG. 5. In some examples, the first frequency is greater than or equal to about 1,000 Hertz and less than or equal to about 5,000 Hertz. In other examples, the first frequency is 1,000 Hertz. Processing circuitry 210 receives, via telemetry circuitry 208, a signal indicative of a urinary activity of patient 112 (404), as described above with respect to FIG. 4. In alternative examples, instead of detecting a urinary activity of the patient, processing circuitry 210 may receive, from sensors 106, a signal indicating spatial, locational, or temporal information about patient 112. In still further examples, instead of detecting a urinary activity of the patient, processing circuitry 210 may receive feedback from patient 112 indicating the commencement of urinary activity.

In response to the detected urinary activity, processing circuitry 210 of IMD 102 controls stimulation generator 202 to interleave the first electrical stimulation pulses at the first frequency greater than or equal to about 100 Hertz and less than or equal to about 20,000 Hertz and the second electrical stimulation pulses at a second frequency greater than or equal to about 1 Hertz and less than or equal to about 50 Hertz (606). Processing circuitry 210 of IMD 102 further controls stimulation generator 202 to deliver electrical stimulation according to the interleaved first electrical stimulation pulses and second electrical stimulation pulses to patient 112. In some examples, processing circuitry 210 of IMD 102 gradually increases one of a voltage amplitude or a current amplitude of the second electrical stimulation pulses so as to prevent discomfort or side effects in patient 112 due to rapid changes in the electrical stimulation therapy.

As described above with respect to FIG. 5, in response to detecting that the urinary activity has ceased (508), processing circuitry 210 of IMD 102 controls stimulation generator 202 to cease delivery of the electrical stimulation therapy comprising the second electrical stimulation pulses, but continues delivery of electrical stimulation therapy comprising the first electrical stimulation pulses (502). In some examples, processing circuitry 210 of IMD 102 gradually decreases one of a voltage amplitude or a current amplitude of the second electrical stimulation pulses so as to prevent discomfort or side effects in patient 112 due to rapid changes in the electrical stimulation therapy. In alternative examples, processing circuitry 210 of IMD 102 continues delivery of the electrical stimulation therapy comprising the interleaved first and second electrical stimulation pulses for a predetermined time. Upon expiration of the predetermined time, processing circuitry 210 of IMD 102 controls stimulation generator 202 to cease delivery of the electrical stimulation therapy comprising the second electrical stimulation pulses and deliver electrical stimulation therapy comprising the first electrical stimulation pulses (502).

FIGS. 7A-7D are timing diagrams depicting example electrical stimulation therapies that the IMD of FIG. 1 delivers to the patient. For ease of description, FIGS. 7A-7D are described with respect to FIGS. 1 and 2. FIGS. 7A-7D depict electrical stimulation therapies that IMD 102 delivers to patient 112. The x-axis of FIGS. 7A-7D denotes time, while the y-axis of FIGS. 7A-7D denote the frequency of the electrical stimulation therapies.

Figure 7A:
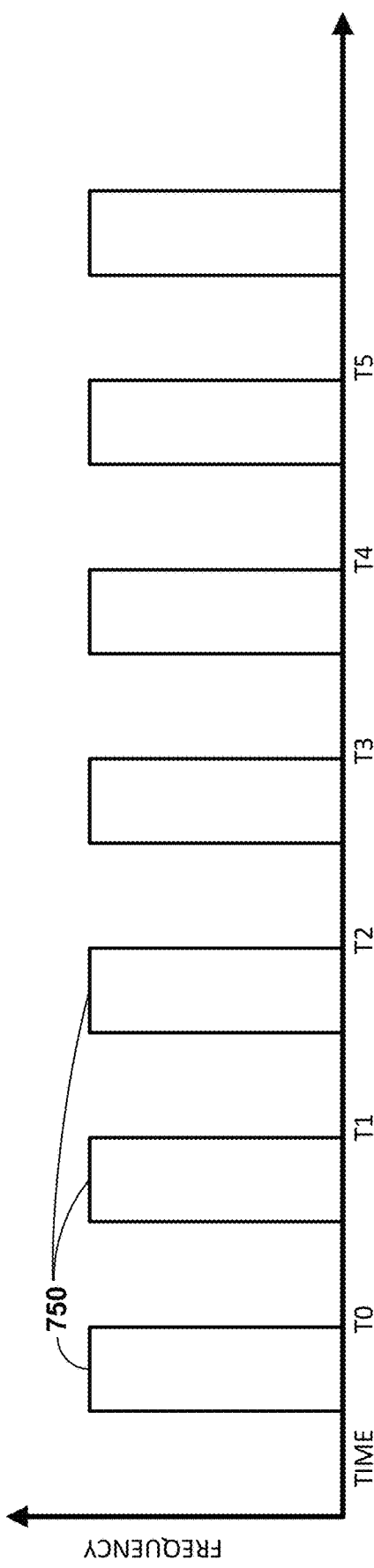

With respect to FIG. 7A, processing circuitry 210 of IMD 102 controls stimulation generator 202 to deliver, to patient 112, first electrical stimulation pulses 750 having a high frequency (e.g., a frequency greater than or equal to about 100 Hertz), and to interleave such first electrical stimulation pulses with periods of no electrical stimulation. In some examples, the high frequency is greater than or equal to about 1,000 Hertz and less than or equal to 5,000 Hertz. In doing so, IMD 102 may deliver electrical stimulation having a high frequency to patient 112 to provide therapy for one or more pelvic symptoms of patient 11.

Figure 7B:
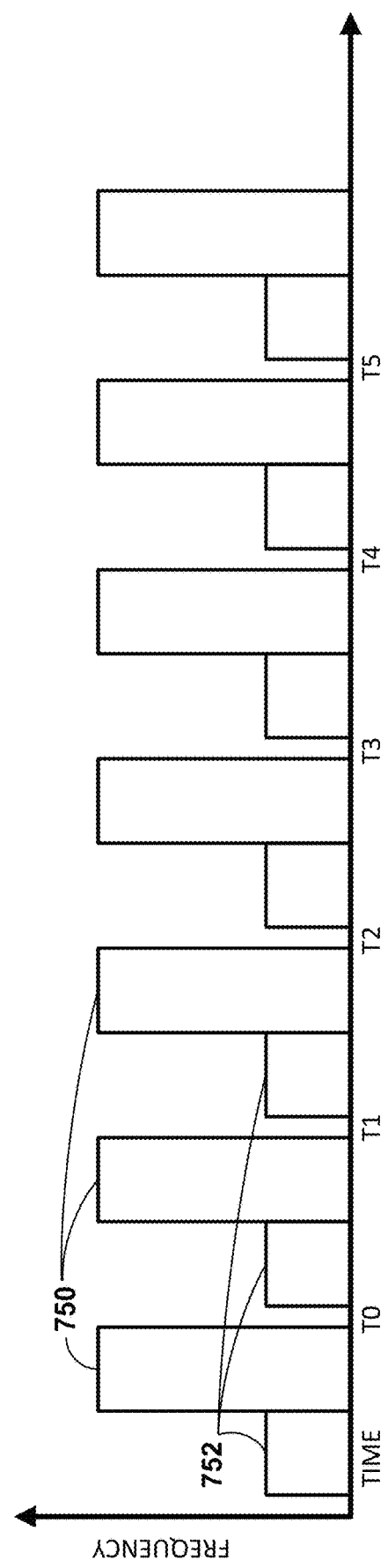

With respect to FIG. 7B, processing circuitry 210 of IMD 102 controls stimulation generator 202 to interleave first electrical stimulation pulses 750 having a high frequency (e.g., a frequency greater than or equal to about 100 Hertz) and second electrical stimulation therapy pulses 752 having a low frequency (e.g., a frequency less than or equal to about 50 Hertz), and deliver the interleaved first and second electrical stimulation pulses to patient 112. In doing so, 102 may provide therapy for one or more pelvic symptoms of patient 112.

With respect to FIG. 7C, processing circuitry 210 of IMD 102 controls stimulation generator 202 to continuously deliver first electrical stimulation therapy pulses 752 having a high frequency (e.g., a frequency greater than or equal to about 100 Hertz) to patient 112. At time T2, one or more sensors 106 of system 100 detects an onset 754 of a urinary activity of patient 112, e.g., a voiding event. In response to detecting the onset 754 of the urinary activity, processing circuitry 210 of IMD 102 controls stimulation generator 202 to cease delivery of the first electrical stimulation therapy pulses 752 and commence delivery of second electrical stimulation pulses 750 having a low frequency (e.g. a frequency less than or equal to about 50 Hertz) to patient 112. At time T5, one or more sensors 106 of system 100 detects a cessation 756 of the urinary activity of patient 112. In response to detecting the cessation 756 of the urinary activity, processing circuitry 210 of IMD 102 controls stimulation generator 202 to cease delivery of the second electrical stimulation therapy pulses 750 and resume delivery of first electrical stimulation pulses 752 to patient 112.

The first electrical stimulation pulses having the high frequency may promote increased bladder capacity, or otherwise assist with the storage of urine in patient 112, but the second electrical stimulation pulses having the low frequency may promote bladder voiding in patient 112. Accordingly, IMD 102 may deliver the first electrical stimulation pulses having the high frequency to promote bladder control in patient 112. Further, upon detecting that patient 112 is undergoing a urinary activity, IMD 102 may switch to delivery of the second electrical stimulation pulses having the low frequency to assist patient 112 in bladder voiding. In particular, varying the frequency of low-frequency stimulation has been shown to change whether the stimulation inhibits bladder contractions or activates the bladder to promote micturition. As a nonlimiting example, stimulation of the dorsal nerve of the penis was shown to inhibit at 5 Hertz to 10 Hertz and activate at 20 Hertz to 40 Hertz.

With respect to FIG. 7D, processing circuitry 210 of IMD 102 controls stimulation generator 202 to continuously deliver first electrical stimulation therapy pulses 752 having a high frequency (e.g., a frequency greater than about 100 Hertz) to patient 112. At time T2, one or more sensors 106 of system 100 detects an onset 754 of a urinary activity of patient 112, e.g., a voiding event. In response to detecting the onset 754 of the urinary activity, processing circuitry 210 of IMD 102 controls stimulation generator 202 to interleave first electrical stimulation pulses 750 having the high frequency with second electrical stimulation therapy pulses 752 having a low frequency (e.g., a frequency less than or equal to about 50 Hertz) and deliver the interleaved first and second electrical stimulation pulses to patient 112. In some examples, processing circuitry 210 controls stimulation generator 202 to gradually increase one of a current amplitude or a voltage amplitude of the second electrical stimulation pulses when transitioning from delivery of the first electrical stimulation pulses and not the second electrical stimulation pulses to delivery of the interleaved first electrical stimulation pulses and second electrical stimulation pulses. At time T5, one or more sensors 106 of system 100 detects a cessation 756 of the urinary activity of patient 112. In response to detecting the cessation 756 of the urinary activity, processing circuitry 210 of IMD 102 controls stimulation generator 202 to cease delivery of the second electrical stimulation therapy pulses 750 and resume delivery of only the first electrical stimulation pulses 752 to patient 112. In some examples, processing circuitry 210 controls stimulation generator 202 to gradually decrease the one of a current amplitude or a voltage amplitude of the second electrical stimulation pulses when transitioning from delivery of the interleaved first electrical stimulation pulses and second electrical stimulation pulses to delivery of only the first electrical stimulation pulses and not the second electrical stimulation pulses.

FIGS. 8A-8B, 9, and 10A-10C depict data from an example study wherein an electrical stimulation device delivers electrical stimulation therapies to a plurality of rat test subjects. The electrical stimulation device delivers electrical stimulation in a fashion substantially similar to IMD 102 of FIG. 1. Other systems deliver sacral neuromodulation for pelvic disorders in the low Hertz range. However, there has been little investigation into the effects of high frequency stimulation. In the study corresponding to the data depicted in FIG. 9, the effect of 1,000 Hertz stimulation was tested on the rhythmic bladder contraction (RBC) model in anesthetized rats. Results demonstrate that high frequency stimulation, such as 1,000 Hertz stimulation, significantly inhibits RBC frequency, though multiple response patterns were seen in different rats. Overall, this data suggests that high frequency stimulation could be effective in altering bladder function. Furthermore, it has been determined that electrical stimulation comprising a frequency greater than 5,000 Hertz may be less effective at inhibiting bladder contractions and consume more power than electrical stimulation comprising a frequency within a range of about 1,000 Hertz to 5,000 Hertz. Thus, this data suggests that electrical stimulation comprising a frequency within a range of about 1,000 Hertz to about 5,000 Hertz provides multiple benefits over either conventional, low frequency electrical stimulation or electrical stimulation electrical stimulation comprising a frequency greater than 5,000 Hertz.

Typically, other systems deliver sacral neuromodulation in the low Hertz range, e.g., 10 to 25 Hertz, because others understand a range of low frequencies to be most effective. For example, the responsiveness of a patient to varying frequencies of electrical stimulation may be visualized as a U-shaped curve. Typically, the muscles of a patient displaying responsiveness to electrical stimulation at frequencies of about 1 to 50 Hertz, displaying limited responsiveness to electrical stimulation at frequencies of about 50 to 100 Hertz, and displaying increasing responsiveness to electrical stimulation at frequencies greater than about 100 Hertz. However, very little is known about very high frequencies in the kilohertz range (e.g., the right end of the U-shaped curve). The present study examined the effect of 1,000 Hertz (1 kilohertz) on the rhythmic bladder contraction (RBC) model in anesthetized rats. The results indicate that 1 kilohertz does have an inhibitory effect on RBC. Similar to stimulation at lower frequencies, this effect is largely inhibiting RBC frequency and not amplitude. Interestingly, the inhibitory effect did not appear in all test subjects, and in some animals a prolonged inhibition followed the 10-minute stimulation period. Overall, these results suggest that stimulation in the kilohertz frequency range provides increased therapeutic efficacy for reducing OAB symptoms over conventional, low frequency electrical stimulation. Furthermore, it has been determined that electrical stimulation at a frequency within a range of about 1,000 Hertz to 5,000 Hertz may provide one or more therapeutic advantages as well as increased power efficiencies relative to stimulation at higher frequencies.

In the study, 16 female Sprague-Dawley rats weighing 200-300 grams received anesthesia (e.g., two injections of urethane spaced 4 minutes apart, with a total dosage of 1.2 grams per kilogram) and maintained during surgery with isoflurane as needed. A heating pad kept a temperature of the rats at 37° C. After the experimental procedures were completed, the rats were euthanized by $CO_2$ asphyxia. Animal Care and Use Committee of Medtronic and Non-Clinical Research Board of Medtronic (Minneapolis, Minn.) approved the experimental protocols of this study. 9 of the 16 rats functioned as a control group, while 7 of the 16 rats received electrical stimulation of the spinal nerve (SN) at 1,000 Hertz.

A cannula (PE50) inserted into the bladder of each rat via the urethra and the urethra was ligated closed with suture to allow recording of the bladder contractions of the rat. The urethral cannula connected to a low-volume pressure transducer of a data acquisition system (ADInstrument MLT0380D, Colorado Springs, Colo., USA) via a T-type connector and the signal was amplified and recorded by a data acquisition system (Spike2; Cambridge Electronic Design). A DC amplifier (AD Instrument, ML119) processed the received signal indicating intravesical pressure. A syringe pump connected to a third output of the T-connector.

The spine of each rat was exposed at the L6 level, the spinal nerve where the majority of bladder afferents enter the spinal cord. Stainless steel wire electrodes were placed bilaterally around the left and right L6 spinal nerves (SN) and fixed with silicone adhesive. Two needle electrodes were placed in the base of the tail to serve as the anode.

The skin around the dorsal sacral and thoracic area was shaved and a dorsal midline incision was made from about SN L3 to S2 to expose the L6/S1 posterior processes. The S1 processes were removed and the L6 nerve trunks localized caudal and medial to the sacroiliac junction. After placing the wire electrode under each nerve, silicone adhesive (Kwik-Cast, World Precision Instruments, Inc., FL, USA) was applied to cover the wire around the nerve, and the skin incision was sutured shut. The electrode connected to the electrical stimulation generator via a stimulus isolation unit (SIU-BI, Grass Medical Instruments). A needle electrode under the skin of the tail acted as ground. The electrical stimulation generator delivered pulses of electrical stimulation to both nerves of each rat serially.

An electrical stimulation generator (e.g., a Grass S88 stimulator) delivered electrical stimulation to the rats via the wire electrodes. Biphasic pulses were set to a frequency of 1 kilohertz, a pulse width of 100 microseconds, and an amplitude of motor threshold (first sign of either pelvic or toe contractions) at 10 Hertz. In two instances, motor threshold for 10 Hertz and 1 kilohertz was directly compared and were within 0.05 milliamps across the two frequencies. After induction of RBC, a baseline period of 15 minutes was followed by 10 minutes of stimulation and 20 minutes of post stimulation. Animals received a maximum of two stimulation trials.

Infusion of saline (50 or 10 microliters per minute) via the syringe connected to a perfusion pump was used to induce a micturition reflex (here defined as bladder contraction of a magnitude>10 mmHg). The infusion rate was then lowered to 10 microliters per minute and continued until 3-5 consecutive contractions occurred. At this time, bladder reflex contractions (BRC) continued after saline infusion terminated. After a 15-minute control period, the electrical stimulation generator delivered electrical stimulation to the SNs for 15 minutes and the BRC were recorded for 20 minutes after the electrical stimulation.

RBC frequency was normalized and compared as number of contractions second (total number of contractions time period). Data are expressed as mean±SEM and were analyzed with Student t-test (Sigma Plot). A p value<0.05 was considered statistically significant.

Electrical stimulation of the SN evoked hind-toe twitches and/or pelvic floor muscle contraction. The threshold current ($T_{mot}$) was defined as the lowest intensity to evoke the first, barely discernable, skeletal muscle contraction. Biphasic pulses having an amplitude of $T_{mot}$ having a pulse width of 0.1 milliseconds stimulated the SN at the frequency of 1,000 Hertz.

Figure 8A:
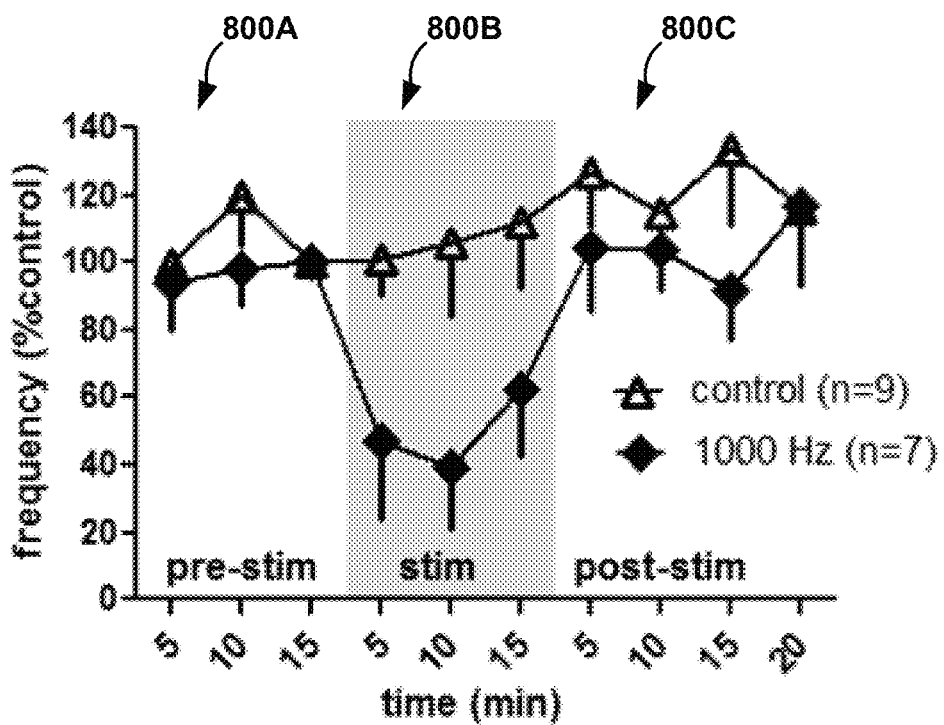
FIGS. 8A-8B are graphs depicting example data of a study wherein an electrical stimulation device delivers electrical stimulation therapies to a plurality of rat test subjects.
Figure 8B:
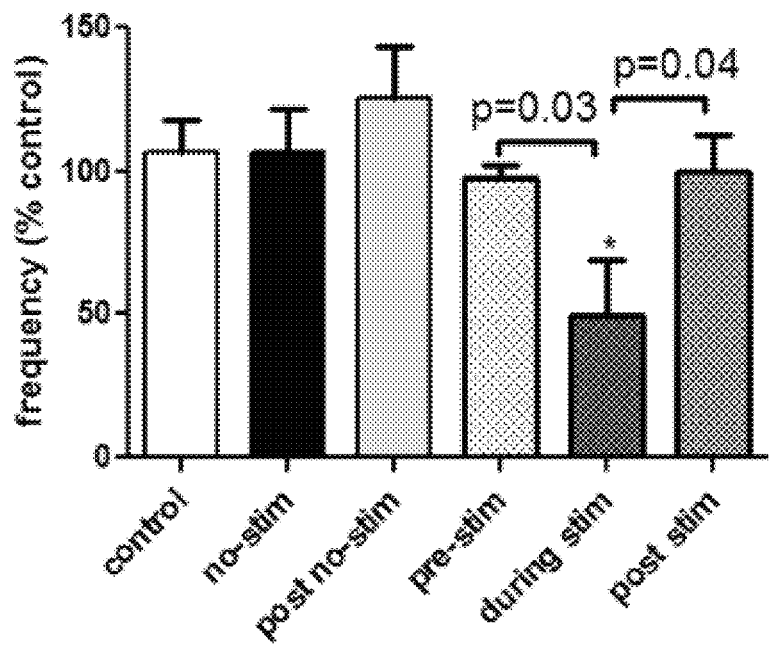

FIGS. 8A-8B are graphs depicting example results of the study. As depicted in FIG. 8A, the frequency of BRC was monitored in 5 minute intervals. A first group 800A of intervals included three control periods. A second group 800B of intervals included three periods during stimulation. A third group 800C of intervals included four periods after stimulation. All data were compared to the mean response during the last 5 minutes prior to stimulation. All data are expressed as mean±SEM. Results were analyzed with Student's t-test by Prism 4 (GraphPad Software, Inc., San Diego, Calif.). A value of p<0.05 was considered statistically significant.

The study determined that no significant change in BRC occurred during a 50-minute period if electrical stimulation was not applied (e.g., for the control group). Further, the study determined that electrical stimulation of the SN at 1,000 Hertz having a pulse width of 0.1 milliseconds and an amplitude of $T_{mot}$ attenuated the frequency of bladder contractions. FIG. 8A depicts the effects of SN stimulation at a motor threshold on the frequency of the BRC for the rats receiving electrical stimulation and the control group (not receiving SN stimulation). BRC responses are represented as a percentage of control (% control), wherein the baseline response of each of the rats prior to receiving electrical stimulation is defined as 100%. In FIG. 8A, the electrical stimulation has a frequency of 1,000 Hertz and a pulse width of 0.1 milliseconds.

FIG. 8B depicts a comparison of 15-minute mean responses of pre-stimulation, during stimulation, and post-stimulation for the control group and the rats receiving electrical stimulation. For the study, p was determined to be less than 0.05. The student's t-test analysis demonstrates that SN stimulation at 1,000 Hertz significantly inhibits BRC frequency.

Figure 9:
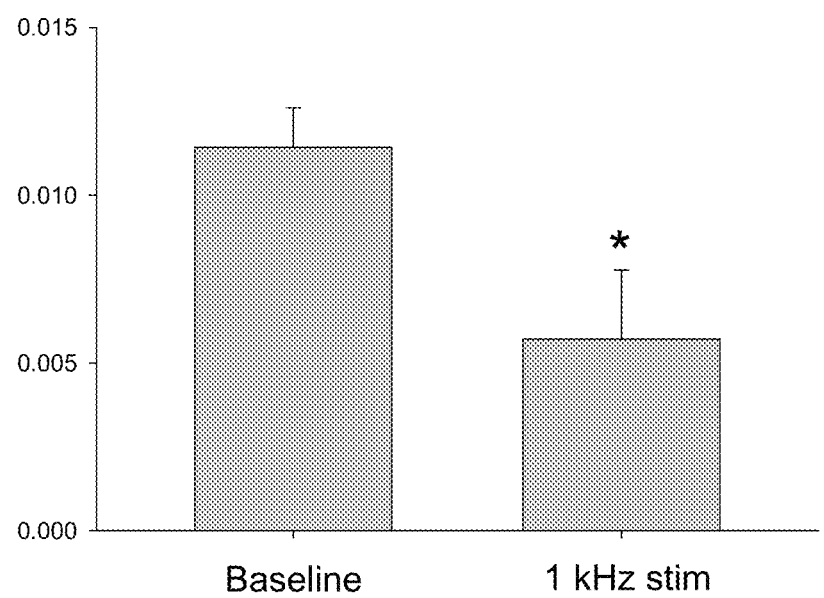
FIG. 9 is a graph depicting example data of the study of FIG. 8.

FIG. 9 is a graph depicting example results of the study. As depicted in FIG. 9, frequency stimulation significantly inhibited ongoing rhythmic bladder contractions. In FIG. 9, the baseline is the contractions per second for the 15-minute period prior to stimulation and "1 kHz stim" is the contractions per second for the 10-minute stimulation period. Error (p) was determined to be less than 0.05, and 7 rats were in the test group.

Figure 10A:
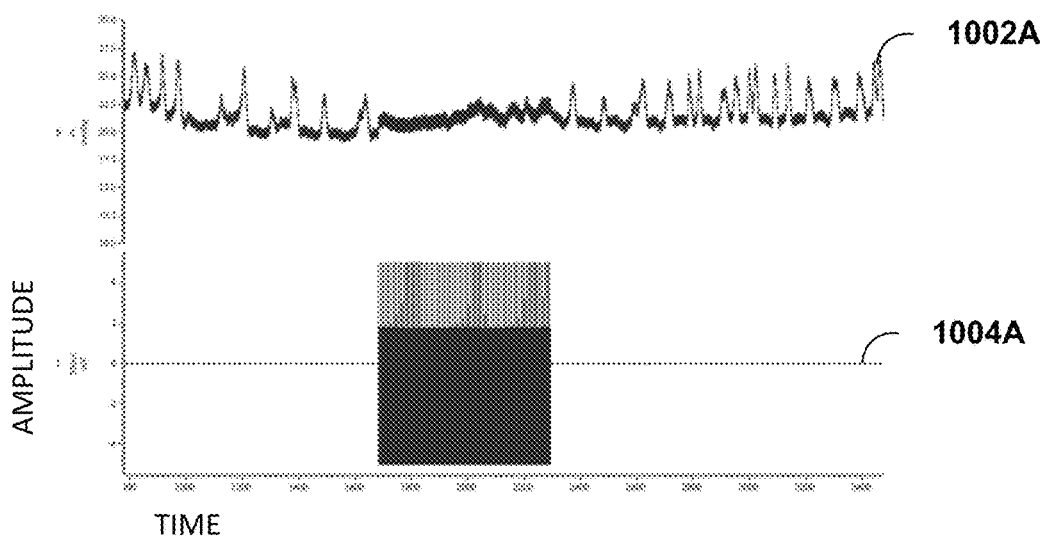
FIGS. 10A-10C are timing diagrams depicting example data of the study of FIG. 8.
Figure 10B:
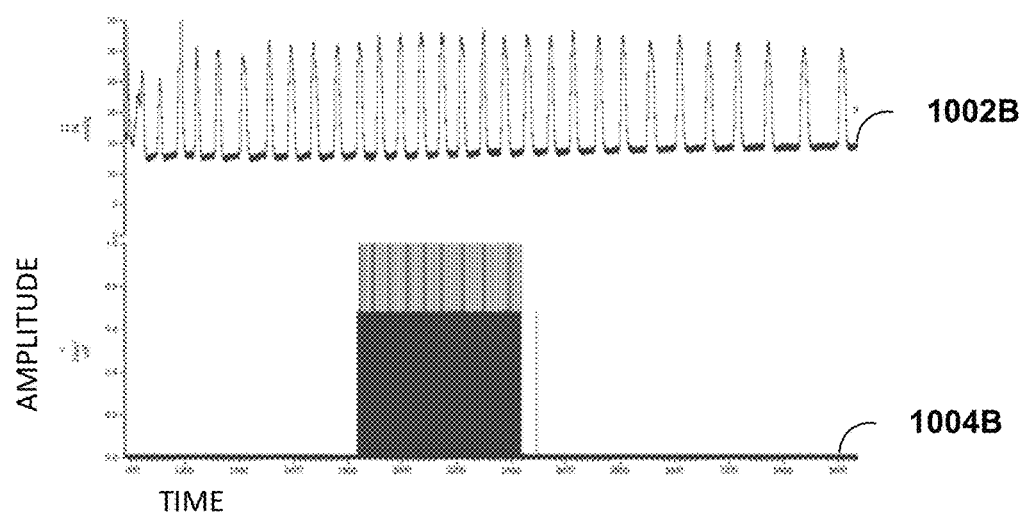
Figure 10C:
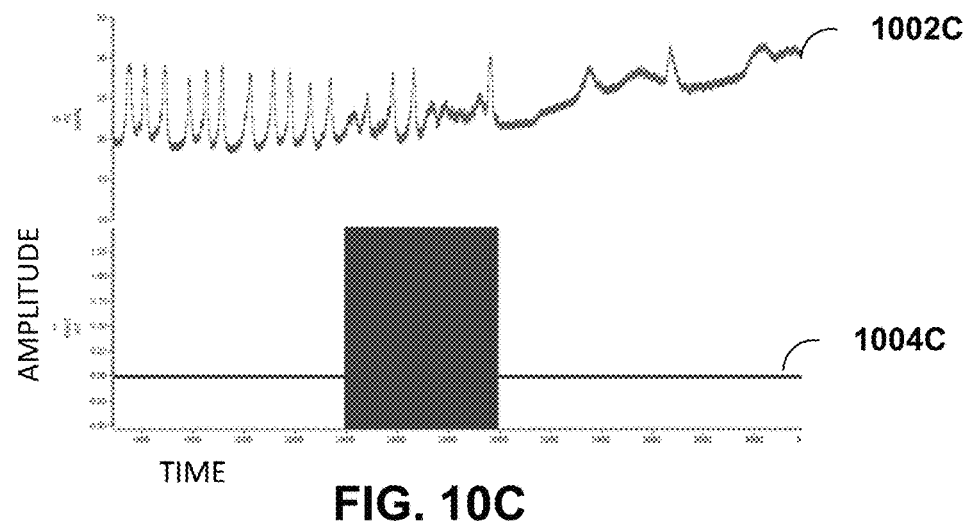

FIGS. 10A-10C are timing diagrams depicting example results of the study. Specifically, FIGS. 10A-10C illustrate the diversity of response patterns to 1 kilohertz stimulation. FIG. 10A shows a trace illustrating inhibition during stimulation for one of the test rats. Two of the seven test rats displayed such acute inhibition of BRC while receiving electrical stimulation (n=2). In this example, the test subjects received electrical stimulation at a frequency of 1 kilohertz, an amplitude of $T_{mot}$, and a pulse width of 210 microseconds for 10 minutes, which acutely inhibited RBC. Upper panel 1002A depicts bladder pressure (mmHg) for the test rat, while lower panel 1004A depicts a timing diagram of the electrical stimulation. The x-axis of FIG. 10A is time in seconds.

FIG. 10B displays a trial with no effect of stimulation on RBC. Two of the test rats displayed no effect on RBC while receiving electrical stimulation (n=2). In this example, the test subjects received electrical stimulation at a frequency of 1 kilohertz, an amplitude of $T_{mot}$, and a pulse width of 210 microseconds for 10 minutes and displayed no effect on RBC. Upper panel 1002B depicts bladder pressure (mmHg) for the test rat, while lower panel 1004B depicts a timing diagram of the electrical stimulation. The x-axis of FIG. 10B is time in seconds.

FIG. 10C depicts an example of prolonged inhibition of BRC even after termination of the electrical stimulation. Three of the test rats displayed such prolonged inhibition of BRC while receiving electrical stimulation (n=3). In this example, the test subjects received electrical stimulation at a frequency of 1 kilohertz, an amplitude of $T_{mot}$, and a pulse width of 210 microseconds for 10 minutes, which evoked a prolonged inhibition of RBC, even after electrical stimulation was removed. Upper panel 1002C depicts bladder pressure (mmHg) for the test rat, while lower panel 1004C depicts a timing diagram of the electrical stimulation. The x-axis of FIG. 10C is time in seconds.

For five of the group of seven rats, the bladder contractions were significantly inhibited during the ten-minute stimulation period compared to the baseline contraction frequency (p=0.033). As a general rule, the amplitude of contractions was not altered, though in individual cases the occasional contraction during or after stimulation showed a reduced amplitude (e.g., as depicted in FIG. 10C).

The results of the study indicate that high-frequency (kilohertz range) stimulation can be an effective parameter range to inhibit bladder contractions. The existence of a 'double-dip' of inhibition of RBC at extremely high frequencies after a range of ineffective parameters (e.g., greater than about 50-100 Hertz and less than about 1 Kilohertz) suggests separate mechanisms of action for stimulation at low Hertz (5-30 Hertz) and high (Kilohertz) frequencies.

Figure 11:
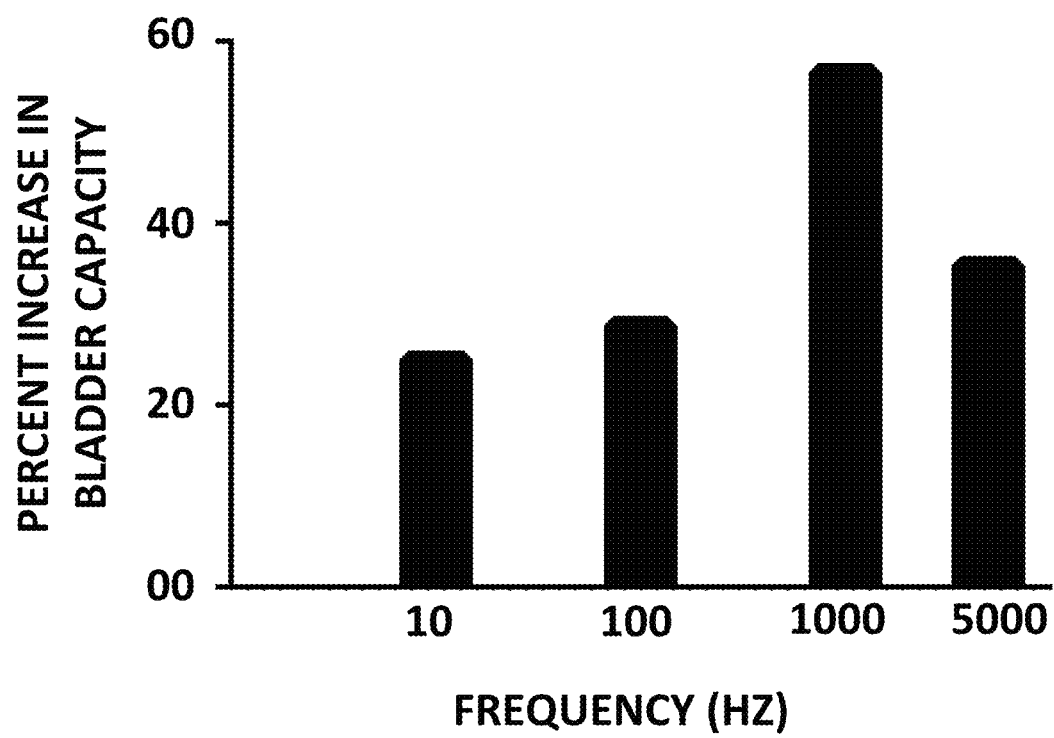
FIG. 11 is a chart depicting bladder capacity as a function of electrical stimulation frequency in an example study of the techniques of the disclosure using sheep test subjects.

FIG. 11 is a chart depicting bladder capacity as a function of electrical stimulation frequency in an example study of the techniques of the disclosure using fully conscious sheep test subjects. In the example of FIG. 11, electrical stimulation was delivered to a plurality of test sheep at frequencies of 10 Hertz, 100 Hertz, 1,000 Hertz, and 5,000 Hertz, and the resultant percent increase in bladder capacity was determined. As depicted in FIG. 11, electrical stimulation delivered at a frequency of 10 Hertz evoked approximately a 20% increase in bladder capacity over the baseline bladder capacity of the test subjects. Further, electrical stimulation delivered at a frequency of 100 Hertz evoked approximately a 30% increase in bladder capacity over the baseline bladder capacity of the test subjects. Further, electrical stimulation delivered at 1,000 Hertz (e.g., a relatively high frequency) evoked approximately a 70% increase in bladder capacity over the baseline bladder capacity of the test subjects, which is a significant 3.5 fold improvement of the baseline bladder capacity over low frequency electrical stimulation (e.g., about 10 Hertz) used in other clinical devices. Accordingly, electrical stimulation having a high frequency (e.g., greater than 100 Hertz) may provide greater increases in bladder capacity as compared to electrical stimulation having a low frequency (e.g., frequencies less than about 50 Hertz). The effect size of 1000 Hertz stimulation on increasing bladder capacity was a surprising result. Without being limited by theory, it is believed that anesthetization of animal subjects in prior studies could have played a role in the failure to previously identify this surprising result. Further, electrical stimulation delivered at a frequency of 5,000 Hertz evoked approximately a 35% increase in bladder capacity over the baseline bladder capacity of the test subjects. Notably, the electrical stimulation delivered at the frequency of 5,000 Hertz was less effective than the electrical stimulation delivered at the frequency of 1,000 Hertz. Based on these results, it is anticipated that as the frequency of electrical stimulation increases beyond 5,000 Hertz, the efficacy of the electrical stimulation may diminish. Thus, the bladder capacity has been shown to increase for electrical stimulation having a frequency greater than or equal to 100 Hertz and less than or equal to 5,000 Hertz unexpectedly provides greater increases in bladder capacity as compared to electrical stimulation at 10 Hertz. While the relative capacity at 5,000 Hertz suggests that frequencies above 5,000 Hertz are less likely to exhibit meaningful (if any) improvements over electrical stimulation at 10 Hertz.

Figure 12:
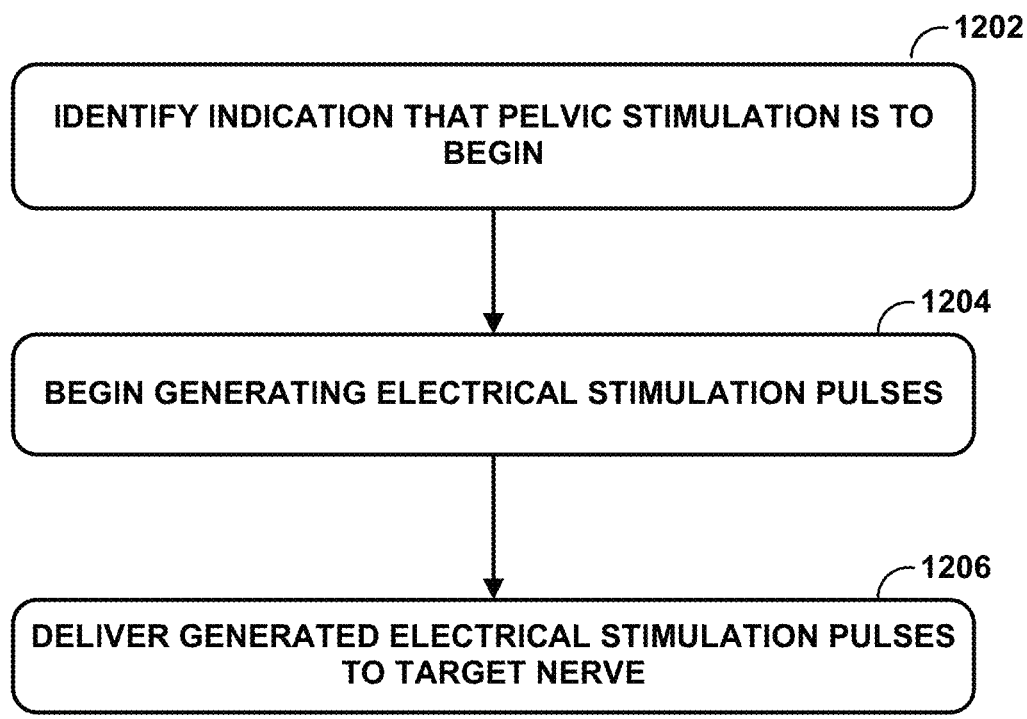
FIG. 12 is a flowchart depicting an example operation of a medical device in accordance with the techniques of the disclosure.

FIG. 12 is a flowchart depicting an example operation of a medical device in accordance with the techniques of the disclosure. In one example, the medical device is IMD 102 of FIG. 1 and is configured to treat one or more pelvic disorders of a human patient 112 consistent with the techniques of the disclosure. In this example, IMD 102 is designed for (at least partial) implantation such that one or more electrodes 116, 118 are placed proximate to a nerve relevant to the treatment of pelvic disorders, such as at least one of a sacral nerve, dorsal nerve of the penis, dorsal nerve of the clitoris, or a pudendal nerve. In other examples, the medical device is an external stimulator device with one or more implanted leads. As discussed herein, the nerve may include any one of the sacral nerve, pelvic nerve, tibial nerve, and the pudendal nerve of patient 112. For example, the medical device may include a stimulation lead having a length, electrode configuration, or other factors, designed for use with one or more of the above identified nerves. Moreover, the medical device may include stimulation circuitry that is configured to provide stimulation consistent with the therapeutic treatment of one or more pelvic disorder. For example, the stimulation circuitry may include a stimulation generator circuit that is designed to generate electrical stimulation pulses at frequencies discussed herein and with (current or voltage) amplitudes sufficient to treat the one or more pelvic disorder. Moreover, processing circuitry of the medical device may be configured to control the timing and other parameters relevant to delivery of the electrical stimulation.

In one example with respect to IMD 102 of FIG. 1, processing circuitry of IMD 102 is configured to identify an indication that pelvic stimulation is to begin (1202). In some examples, the indication indicates the start of inhibition of bladder activity. In some examples, the processing circuitry of IMD 102 receives the indication from external programmer 104. In one example where external programmer 104 is a patient programmer, the patient programmer may include an option for patient 112 to enable and disable stimulation (e.g., to manually intimate voiding of the bladder). In one example where external programmer 104 is a clinician programmer, the clinician may use the clinician programmer to provide to IMD 102 a stimulation schedule that defines when to begin or end pelvic stimulation. The processing circuitry of IMD 102 may identify indications from the stimulation schedule to control the start and end of electrical stimulation. As another example, the processing circuitry of IMD 102 may receive data from one or more sensors and use the data to identify an event, such as the beginning or end of urinary activity, that indicates when to start inhibition of bladder activity.

In response to identifying the indication, the processing circuitry of IMD 102 begins generating electrical stimulation pulses (1204). In accordance with the techniques of the disclosure, IMD 102 may generate the electrical stimulation pulses to provide improved bladder capacity by using frequencies exceeding 100 Hertz. In one example, IMD 102 generates the electrical stimulation pulses at a frequency greater than or equal to 500 Hertz and less than or equal to 5,000 Hertz, or within other frequency ranges discussed herein. IMD 102 delivers the generated stimulation pulses to the targeted nerve (1206). In the example of FIG. 1, IMD 102 delivers the generated stimulation pulses using electrodes 116, 118 placed proximate to the targeted nerve.

In some examples, IMD 102 is configured to deliver electrical stimulation at different frequencies depending upon the type of identified event. As one example, the identification carried out with respect to block 1202 identifies that the bladder is to be stimulated to induce micturition. IMD 102 may adjust the electrical stimulation generated in block 1204 accordingly (e.g., to around 30 Hertz) before being delivered per block 1206.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components.

The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuitry, modules or components may be implemented together or separately as discrete but interoperable logic devices. Depiction of different features as circuitry, modules, or units is intended to highlight different functional aspects and does not necessarily imply that such circuitry, modules, or units must be realized by separate hardware or software components. Rather, functionality associated with one or more circuits, modules, or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method for delivering electrical stimulation with a medical device configured to be at least partially implanted in a patient, the method comprising:
    identifying, by the medical device, an indication to inhibit at least one of a bladder contraction event or a bladder voiding event;
    generating, by the medical device and in response to identifying the indication, electrical stimulation therapy comprising first electrical stimulation pulses comprising a first frequency greater than or equal to about 1,000 Hertz and less than or equal to about 5,000 Hertz; and
    delivering, by the medical device, the electrical stimulation therapy to a target nerve selected from a group consisting of: a sacral nerve, a pelvic nerve, a tibial nerve, and a pudendal nerve of the patient.

2. The method of claim 1, wherein the electrical stimulation therapy further comprises second electrical stimulation pulses comprising a second frequency greater than or equal to about 1 Hertz and less than or equal to about 50 Hertz, wherein the second electrical stimulation pulses are interleaved with the first electrical stimulation pulses.

3. The method of claim 2, wherein identifying the indication comprises detecting, via one or more sensors, a presence or absence of the at least one of the bladder contraction event or the bladder voiding event.

4. The method of claim 3, further comprising:
    delivering, in response to detecting the absence of the at least one of the bladder contraction event or the bladder voiding event, the first electrical stimulation pulses; and
    delivering, in response to detecting the at least one of the bladder contraction event or the bladder voiding event of the patient, the second electrical stimulation pulses.

5. The method of claim 4, further comprising: gradually increasing one of a current amplitude or a voltage amplitude of the second electrical stimulation pulses when transitioning from delivery of the first electrical stimulation pulses to delivery of the second electrical stimulation pulses.

6. The method of claim 4, wherein the indication to inhibit the at least one of the bladder contraction event or the bladder voiding event comprises
    a feedback received from the patient.

7. The method of claim 2, further comprising:
    delivering, by the medical device, the first electrical stimulation pulses and not the second electrical stimulation pulses;
    receiving, by the medical device and from an external programmer, feedback from the patient; and
    delivering, in response to the feedback and by the medical device, the second electrical stimulation pulses and not the first electrical stimulation pulses.

8. The method of claim 1, further comprising adjusting the first frequency in response to feedback from the patient.

9. The method of claim 1, further comprising:
    detecting, by sensing circuitry of a medical system comprising the medical device, a spatial location of the patient; and
    adjusting the generating of the electrical stimulation therapy comprising the first electrical stimulation pulses based on the detected spatial location of the patient.

10. The method of claim 1, further comprising:
    detecting, by sensing circuitry of a medical system comprising the medical device, a posture of the patient; and
    adjusting the generating of the electrical stimulation therapy comprising the first electrical stimulation pulses based on the detected posture of the patient.

11. The method of claim 1, further comprising:
    detecting, by sensing circuitry of a medical system comprising the medical device, a time of day; and
    adjusting the generating of the electrical stimulation therapy comprising the first electrical stimulation pulses based on the detected time of day.

12. The method of claim 1, further comprising:
    detecting, by sensing circuitry of a medical system comprising the medical device, electrical activity of a tissue of the patient; and
    adjusting the generating of the electrical stimulation therapy comprising the first electrical stimulation pulses based on the detected electrical activity of the tissue of the patient.

13. The method of claim 1, further comprising:
    detecting, by sensing circuitry of a medical system comprising the medical device, a biomarker of the patient indicating at least one of a side effect of delivering the electrical stimulation therapy comprising the first electrical stimulation pulses or an efficacy of a therapeutic effect of delivering the electrical stimulation therapy comprising the first electrical stimulation pulses; and
    adjusting the generating of the electrical stimulation therapy comprising the first electrical stimulation pulses based on the detected biomarker of the patient.

14. The method of claim 1, wherein the target nerve is a sacral nerve of the patient.

15. A medical system comprising a medical device configured to be at least partially implanted in a patient, the medical device comprising:
   a lead including one or more electrodes and configured for placement near a target nerve selected from a group consisting of: a sacral nerve, a pelvic nerve, a tibial nerve, and a pudendal nerve of the patient;
   electrical stimulation generation circuitry configured to generate electrical stimulation therapy comprising first electrical stimulation pulses comprising a first frequency greater than or equal to about 1,000 Hertz and less than or equal to about 5,000 Hertz; and
   processing circuitry configured to:
      identify an indication to inhibit at least one of a bladder contraction event or a bladder voiding event; and
      control the electrical stimulation generation circuitry to deliver the electrical stimulation therapy to the target nerve via the one or more electrodes.

16. The medical system of claim 15, wherein the electrical stimulation therapy further comprises second electrical stimulation pulses comprising a second frequency greater than or equal to about 1 Hertz and less than or equal to about 50 Hertz, wherein the second electrical stimulation pulses are interleaved with the first electrical stimulation pulses.

17. The medical system of claim 16, further comprising one or more sensors, and
   wherein, to identify the indication, the processing circuitry is further configured to detect, via the one or more sensors, the at least one of the bladder contraction event or the bladder voiding event, and wherein the processing circuitry is further configured to detect via the one or more sensors, a presence or absence of the at least one of the bladder contraction event or the bladder voiding event.

18. The medical system of claim 17, wherein the processing circuitry is further configured to:
   in response to detecting the absence of the at least one of the bladder contraction event or the bladder voiding event, control the electrical stimulation generation circuitry to deliver the first electrical stimulation pulses; and
   in response to detecting the at least one of the bladder contraction event or the bladder voiding event of the patient, delivering, control the electrical stimulation generation circuitry to deliver the second electrical stimulation pulses.

19. The medical system of claim 18, wherein the processing circuitry is further configured to control the electrical stimulation generation circuitry to gradually increase one of a current amplitude or a voltage amplitude of the second electrical stimulation pulses when transitioning from delivery of the first electrical stimulation pulses to delivery of the second electrical stimulation pulses.

20. A medical device configured to be at least partially implanted in a patient, the medical device comprising:
   means for identifying an indication to inhibit at least one of a bladder contraction event or a bladder voiding event;
   means for generating, in response to identifying the indication, electrical stimulation therapy comprising first electrical stimulation pulses comprising a first frequency greater than or equal to about 1,000 Hertz and less than or equal to about 5,000 Hertz; and
   means for delivering the electrical stimulation therapy to a target nerve selected from a group consisting of: a sacral nerve, a pelvic nerve, a tibial nerve, and a pudendal nerve of the patient.

\* \* \* \* \*